US012661185B2

(12) United States Patent
Decrouez et al.

(10) Patent No.: US 12,661,185 B2
(45) Date of Patent: Jun. 23, 2026

(54) DEVICE AND METHOD FOR OBTAINING AN AUGMENTED PATIENT-SPECIFIC BONE/CARTILAGE MODEL OF A TARGET ANATOMICAL STRUCTURE OF A PATIENT

(71) Applicant: GANYMED ROBOTICS, Paris (FR)

(72) Inventors: Marion Decrouez, Paris (FR); Anna Gounot, Paris (FR); Valérie Burdin, Paris (FR); Guillaume Dardenne, Paris (FR); Baptiste Dehaine, Paris (FR)

(73) Assignee: GANYMED ROBOTICS, Paris (FR)

( * ) Notice: Subject to any disclaimer, the term of this patent is extended or adjusted under 35 U.S.C. 154(b) by 0 days.

(21) Appl. No.: 19/337,380

(22) Filed: Sep. 23, 2025

(65) Prior Publication Data

US 2026/0076745 A1     Mar. 19, 2026

Related U.S. Application Data

(63) Continuation of application No. PCT/EP2025/051174, filed on Jan. 17, 2025.

(30) Foreign Application Priority Data

Jan. 19, 2024     (EP) ..................................... 24305122

(51) Int. Cl.
*A61B 34/10* (2016.01)
*A61B 90/00* (2016.01)

(52) U.S. Cl.
CPC ........ *A61B 34/10* (2016.02); *A61B 2034/105* (2016.02); *A61B 2034/107* (2016.02); *A61B 2034/108* (2016.02); *A61B 2090/365* (2016.02)

(58) Field of Classification Search
CPC .............. A61B 34/10; A61B 2034/105; A61B 2034/107; A61B 2034/108; A61B 2090/365; A61B 2034/2055; A61B 8/0875; A61B 8/483; A61B 2090/378; A61B 34/20; A61B 2090/367; A61B 5/4504; A61B 8/466; A61B 8/5207; A61B 8/5223; A61B 8/5238; G06T 2207/30008; G06T 2210/41; G06T 7/0012; G06T 17/00; G06T 19/20; G06T 2207/10116;
(Continued)

(56) References Cited

U.S. PATENT DOCUMENTS 11,704,872 B2 *  7/2023  Hu .......................... G06T 19/00
11,717,353 B2 *  8/2023  Zuhars ................... A61B 34/20
                                                                606/86 R
(Continued)

FOREIGN PATENT DOCUMENTS

WO      2020/216934 A1    10/2020

OTHER PUBLICATIONS

Van Dijck et al., "Statistical shape model-based prediction of tibiofemoral cartilage," Computer Methods in Biomechanics and Biomedical Engineering, Oct. 26, 2018, DOI: 10.1080/10255842.2018.1495711.
(Continued)

*Primary Examiner* — Michael S Osinski
(74) *Attorney, Agent, or Firm* — Morgan, Lewis & Bockius LLP

(57)     ABSTRACT

The present invention relates to a device and method for obtaining an augmented patient-specific bone/cartilage model of a target anatomical structure of a patient.

18 Claims, 10 Drawing Sheets

(58) Field of Classification Search

CPC . G06T 2207/10088; G06T 2207/20084; G06T 2207/10081; G06T 2219/2021; G16H 50/20; G16H 50/50; G16H 30/20

See application file for complete search history.

(56) References Cited

U.S. PATENT DOCUMENTS

| | | | | |
|---|---|---|---|---|
| 12,056,822 | B2 * | 8/2024 | Dehaine ................. | G06T 15/06 |
| 12,064,187 | B2 | 8/2024 | Bleunven et al. | |
| 12,133,690 | B2 * | 11/2024 | Pasha ..................... | G16H 20/40 |
| 12,527,546 | B2 * | 1/2026 | Wasielewski ........ | A61B 8/4477 |
| 2003/0032876 | A1 * | 2/2003 | Chen ...................... | G09B 23/28 |
| | | | | 600/407 |
| 2007/0053560 | A1 * | 3/2007 | Miller .................. | G06T 7/0012 |
| | | | | 382/128 |
| 2010/0198067 | A1 * | 8/2010 | Mahfouz ............... | G16H 50/50 |
| | | | | 600/443 |
| 2010/0220907 | A1 * | 9/2010 | Dam ...................... | G06V 10/26 |
| | | | | 382/128 |
| 2010/0256504 | A1 | 10/2010 | Moreau-Gaudry et al. | |
| 2011/0093108 | A1 * | 4/2011 | Ashby ................. | A61F 2/30942 |
| | | | | 703/2 |
| 2013/0144135 | A1 * | 6/2013 | Mahfouz ................ | G06T 19/20 |
| | | | | 600/309 |
| 2014/0163375 | A1 * | 6/2014 | Wasielewski .......... | G16H 50/20 |
| | | | | 600/443 |
| 2016/0279877 | A1 * | 9/2016 | Lavallee .............. | B29C 64/386 |
| 2017/0347991 | A1 * | 12/2017 | Mahfouz .............. | A61B 8/5207 |
| 2023/0071033 | A1 * | 3/2023 | Ehlke .................... | A61B 34/25 |
| 2023/0222651 | A1 * | 7/2023 | Yao ......................... | G06T 17/00 |
| | | | | 382/128 |
| 2023/0368465 | A1 * | 11/2023 | Mahfouz ................ | G06T 17/00 |
| 2024/0090825 | A1 * | 3/2024 | Erdemir .............. | A61B 5/4528 |
| 2024/0096508 | A1 * | 3/2024 | Nikou ................... | A61B 34/10 |
| 2025/0025128 | A1 * | 1/2025 | Chaoui ................... | A61B 8/42 |
| 2025/0120771 | A1 * | 4/2025 | Adams .................. | A61B 34/20 |

OTHER PUBLICATIONS

Van Oevelen et al., "Personalized statistical modeling of soft tissue structures in the knee," Frontiers in Bioengineering and Biotechnology, vol. 11, Mar. 8, 2023, DOI: 10.3389/fbioe.2023.1055860.

European Search Report, completed Jun. 18, 2024, and Written Opinion for European Application No. 24305122.4.

International Search Report and Written Opinion for related International Application No. PCT/EP2025/051174, mailed Apr. 14, 2025, 12 pages.

Peiffer M et al., "Personalised statistical modeling of soft tissue structures in the ankle", Computer Methods and Programs in Biomedicine, Elsevier, Amsterdam, NL, vol. 218, Feb. 17, 2022.

Kumar T. Rajamani et al., "Bone morphing with statistical shape models for enhanced visualization", Proceedings of SPIE, vol. 5367, May 5, 2004, pp. 122-130.

Communication pursuant to Article 94(3) EPC for European Application No. 25700784.9, dated Sep. 3, 2025.

* cited by examiner (a) Healthy train set          (b) Medially pathological train set (a) Healthy train set          (b) Medially pathological train set (a) First mode of healthy models (b) First mode of pathological models (c) Second mode of healthy models (d) Second mode of pathological models (e) Third mode of healthy models (f) Third mode of pathological models (a) Healthy test set (b) Pathological test set (b) Pathological test set (a) Healthy test set

DEVICE AND METHOD FOR OBTAINING AN AUGMENTED PATIENT-SPECIFIC BONE/CARTILAGE MODEL OF A TARGET ANATOMICAL STRUCTURE OF A PATIENT

CROSS-REFERENCE TO RELATED APPLICATIONS

This application is a continuation of International Application No. PCT/EP2025/051174, filed Jan. 17, 2025, which claims priority to and the benefit of European Application No. 24305122.4, filed Jan. 19, 2024, the entirety of each which is incorporated herein by reference.

FIELD OF INVENTION

The present invention relates to the field of medical imaging processing for use during surgery. Notably the invention relates to a device and method for obtaining an augmented patient-specific bone/cartilage model of a target anatomical structure of a patient.

BACKGROUND OF INVENTION

Clinically, obtaining accurate 3D models of the patient's bones is crucial for surgical planning, implant fitting, surgical navigation, robot-assisted surgery, and postoperative evaluation in orthopedics. Nowadays, in most cases, the models are obtained by post-processing 3D medical imaging data such as CT scans and/or MRI.

In orthopedic surgery, precise 3D models of the bones are usually generated from CT images. Nevertheless, the anatomical structures to be operated on (especially joint areas) are covered with a varying thickness of cartilage. The cartilage is a soft tissue mostly made of water: it is not visible in the CT scan and is therefore usually not included in the 3D model.

Yet, the presence of cartilage disturbs the matching of the preoperative model with intraoperative data acquired on exposed bone surface during surgery. This may lead to inaccuracies in the patient intraoperative localization process that are incompatible with the required clinical performances.

In this context, there is a need to develop a 3D patient-specific bone model that includes a cartilage representation, which will reduce errors during the surgery.

SUMMARY

The present invention thus relates to a device for obtaining an augmented patient-specific bone/cartilage model of a target anatomical structure of a patient, said target anatomical structure including at least one portion of a target bone and at least one portion of a target cartilage, said device comprising:

at least one input configured to receive:

a dataset comprising 3D images acquired on a plurality of subjects, each 3D image acquired on a subject comprising a subject anatomical structure corresponding to the target anatomical structure, wherein said 3D images comprise bone tissues of the subject anatomical structure and at least part of said 3D images comprise cartilage tissues of the subject anatomical structure, and a previously generated patient-specific 3D model of at least one portion of said target bone of the patient;

at least one processor configured to:

for at least two 3D images of the dataset, segment the bone tissues of the subject anatomical structure, determine a bone Statistical Shape Model based on said segmented bone tissues, for at least two 3D images of the dataset comprising cartilage tissues of the subject anatomical structure, segment the subject anatomical structure and perform a rigid registration of said bone Statistical Shape Model with the segmented bone tissues of the subject anatomical structure and optimize at least one parameter of said bone Statistical Shape Model to correspond with said bone tissues so as to obtain a global dataset comprising the optimized bone Statistical Shape Model associated with the cartilage tissues from the segmented subject anatomical structure, determine a global Statistical Shape Model of the subject anatomical structure based on said global dataset, said global Statistical Shape Model including a bone portion (e.g., corresponding with said segmented bone tissues of the subject anatomical structure) and a cartilage portion (e.g., portion corresponding with cartilage tissues from said segmented subject anatomical structure), perform a rigid registration of the bone portion from said global Statistical Shape Model with said patient-specific 3D model and optimize at least one parameter of said global Statistical Shape Model to correspond with said patient-specific 3D model, and generate said augmented patient-specific bone/cartilage model of the target anatomical structure based on the optimized global Statistical Shape Model registered with said patient-specific 3D model.

In other words, the invention proposes to alter a patient-specific 3D model of the target bone that needs to be operated on using a generic statistical shape model that includes both bone and cartilage representations. This allows to obtain a more complete 3D patient-specific bone model that also includes a cartilage representation. This is particularly interesting in the context of clinical routine, where only X-rays or CT-scanner images are acquired for patients that have to undergo orthopedic surgery. Indeed, X-rays or CT-scanner are not suitable to capture soft tissues structures such as the cartilage, and can only be used to obtain information on bone tissues and calculate 3D model of the bones. The present invention provides a solution to obtain a patient-specific representation of both bone and cartilage tissues without the need of acquiring extra-routine images (such as MRI images and the like).

Advantageously, the augmented patient-specific bone/cartilage model provides a more accurate representation of the reality. Notably, the augmented patient-specific bone/cartilage model provides additional information on cartilage compared to the bone model obtained preoperatively. Indeed, an accurate representation of the surgical reality is crucial to precisely guide a robotic system that relies on the localization of the target anatomical structure. This especially applies to tracker-less systems that rely on the registration of 3D images of the surgical field with a patient-specific 3D model. Additionally, the obtained 3D patient-specific bone model allows to know the thickness of the cartilage and to remove surgical steps and potential errors, while increasing the accuracy of the overall process. Indeed, usually, during an orthopedic surgery, the cartilage must be completely removed to expose the bone surface. The claimed invention advantageously allows to no longer have to remove cartilage or use palpation devices for registration that go through the cartilage but not the bone. Overall, the device of the invention allows to reduce operating time while also improving registration.

Furthermore, the use of a global Statistical Shape Model that simultaneously represents both bone and cartilage allows for the creation of a more accurate augmented patient-specific bone/cartilage model. With such a global Statistical Shape Model, it is possible to start by deforming the bone and obtain the corresponding most probable cartilage, or conversely, modify the cartilage alone and derive the most probable bone. This approach also enables updating the patient-specific model with data points for both bone and cartilage.

According to other aspects of the invention, the device comprises one or more of the features described in the following embodiments, taken alone or in any possible combination.

According to one embodiment, said dataset comprises:

a first ensemble comprising 3D images acquired from a plurality of subjects, said 3D images comprising bone tissues from the subject anatomical structure, and a second ensemble comprising 3D images acquired from a plurality of subjects, said 3D images comprising bone tissues and cartilage tissues from the subject anatomical structure.

For instance, the first ensemble may comprise X-rays images or CT-scanner images while the second ensemble may comprise MRI images.

Moreover, the previously generated patient-specific 3D model may be directly received as an input by the at least one processor. Alternatively, the patient-specific 3D model may be constructed by the at least one processor in a previous step, based on at least one previously acquired 3D image of the patient comprising at least one portion of the target bone.

According to one embodiment, the at least one input is further configured to receive at least one 3D image acquired from at least one 3D image sensor during surgery, wherein said at least one 3D image represents at least one exposed portion of the target anatomical structure, and wherein the at least one processor is further configured to register and optimize at least one parameter of the augmented patient-specific bone/cartilage model associated to the cartilage with the at least one exposed portion of the target anatomical structure of the 3D image.

According to one embodiment, registering and optimizing the at least one parameter of the augmented patient-specific bone/cartilage model is achieved by minimizing a cost function that takes into account the at least one parameter of the augmented patient-specific bone/cartilage model and localization parameters.

The localization parameters may be parameters of rotation, translation or scaling between the augmented patient-specific bone/cartilage model associated to the cartilage and the at least one exposed portion of the target anatomical structure of the 3D image so that when these parameters are applied (e.g. by a rigid transformation) to one of the augmented patient-specific bone/cartilage model associated to the cartilage and the at least one exposed portion of the target anatomical structure of the 3D image, they correspond as much as possible (e.g. the distance between the two is minimized).

According to one embodiment, determining said global Statistical Shape Model comprises:

defining a plurality of vectors being normal to at least one portion of a surface of said optimized bone Statistical Shape Model of the global dataset;

for each of the segmented cartilage of the global dataset, obtaining a first and a second intersection between each of said plurality of vectors and said segmented cartilage; and determining said global Statistical Shape Model using said first and second intersections, obtained from the plurality of segmented cartilages of the global dataset, and the optimized bone Statistical Shape Model of the third dataset.

According to one embodiment, the input is further configured to receive at least one thickness measurement performed on a predetermined position on the cartilage, and the processor is further configured to constrain the optimization of the at least one parameter of the global Statistical Shape Model associated to the cartilage based on the at least one measurement so as to generate an updated augmented patient-specific bone/cartilage model.

According to the invention, a thickness measurement quantifies the thickness or distance from the joint surface to the underlying cartilage tissue within a specific anatomical region. The thickness measurement may be obtained preoperatively through medical imaging techniques such as magnetic resonance imaging (MRI) or ultrasound, which provide non-invasive and precise assessments of cartilage thickness in various anatomical locations, especially in joints like the knee or hip. Alternatively, the thickness measurement may be performed during surgery using specific palpation tools.

Advantageously, performing the registration with the exposed target anatomical structure using the updated augmented patient-specific bone/cartilage model allows to improve localization of the target. Indeed, the thickness measurements adds some intraoperative data to the augmented patient-specific bone/cartilage model, which is more precise on the real anatomy of the patient compared to statistical information.

According to one embodiment, the input is further configured to receive at least one metadata, and wherein the processor is further configured to constrain the optimization of the at least one parameter of the global Statistical Shape Model based on the at least one metadata so as to generate an updated augmented patient-specific bone/cartilage model.

According to the invention, metadata are statistical data that may be given as an input to the device of the invention in order to constrain the parameters of the global Statistical Shape Model during the optimization step. Such metadata may include the age of a subject, the sex, the Body Mass Index (BMI), the Hip-Knee-Ankle (HKA) angle, the arthrosis grade and/or data on the cartilage such as the thickness at a given position.

According to one embodiment, said at least one processor is further configured to use said augmented patient-specific bone/cartilage model to guide an orthopedic surgery guidance system.

According to one embodiment, said at least one processor is further configured to use the augmented patient-specific bone/cartilage model to choose a suitable implant for the patient or to generate an implant model that is designed specifically for the patient, using for example an adapted CAD software.

Another aspect of the invention pertains to a computer implemented method for obtaining an augmented patient-specific bone/cartilage model of a target anatomical structure of a patient, said target anatomical structure including at least one portion of a target bone and at least one portion of a target cartilage, said method comprising:

receiving:

a dataset comprising 3D images acquired on a plurality of subjects, each 3D image acquired on a subject comprising a subject anatomical structure corresponding to the target anatomical structure, wherein said 3D images comprise bone tissues of the subject anatomical structure and at least part of said 3D images comprise cartilage tissues of the subject anatomical structure, and a previously generated patient-specific 3D model of at least one portion of said target bone of the patient;

for at least two 3D image of the dataset, segmenting the bone tissues of the subject anatomical structure, determining a bone Statistical Shape Model based on said segmented bone tissues, for at least two 3D image of the dataset comprising cartilage tissues of the subject anatomical structure, segmenting the subject anatomical structure and performing a rigid registration of said bone Statistical Shape Model with the segmented bone tissues of the subject anatomical structure and optimizing at least one parameter of said bone Statistical Shape Model to correspond with said bone tissues so as to obtain a global dataset comprising the optimized bone Statistical Shape Model associated with the cartilage tissues from the segmented subject anatomical structure, and determining a global Statistical Shape Model of the at least one portion of target bone and target cartilage of the target anatomical structure based on said global dataset, said global Statistical Shape Model including a bone portion and a cartilage portion, performing a rigid registration of the bone portion from said global Statistical Shape Model with said patient-specific 3D model and optimizing at least one parameter of said global Statistical Shape Model to correspond with said patient-specific 3D model, and generating said augmented patient-specific bone/cartilage model of the target anatomical structure based on the optimized global Statistical Shape Model registered with said patient-specific 3D model.

Another aspect of the invention pertains to a system for obtaining an augmented patient-specific bone/cartilage model of a target anatomical structure of a patient, said target anatomical structure including at least one portion of a target bone and at least one portion of a target cartilage, the system comprising:

one or more memory units each operable to store at least one program; and at least one processor communicatively coupled to the one or more memory units, in which the at least one program, when executed by the at least one processor, causes the at least one processor to:

obtain a bone template model representative of bone tissues from a target anatomical structure of a plurality of target subjects;

obtain a bone/cartilage template model representative of bone and cartilage tissues from the target anatomical structure of a plurality of target subjects;

register the bone template model to the bone/cartilage template model to obtain a combined bone/cartilage template model, and register the combined bone/cartilage template model with a patient-specific bone model to generate the augmented patient-specific bone/cartilage model including the at least one portion of a target bone and the at least one portion of a target cartilage.

According to the invention, a bone template model representative of bone tissues from a target anatomical structure may correspond to the bone Statistical Shape Model as described above.

According to the invention, a bone/cartilage template model representative of bone and cartilage tissues from the target anatomical structure may correspond to the global Statistical Shape Model.

According to one embodiment, the processor is further configured to determine a thickness of the cartilage at one or more points in the augmented patient-specific bone/cartilage model.

According to one embodiment, the processor is further configured to:

obtain intraoperative patient-specific bone/cartilage data representative of the target anatomical structure of the patient during surgery including at least one portion of a target bone and at least one portion of a target cartilage;

register the intraoperative patient-specific bone/cartilage data to the augmented patient-specific bone/cartilage model; and determine that one or more regions where the target anatomical structure of the patient includes an amount of cartilage that meets certain cartilage amount criteria for performing a surgery on the target anatomical structure of the patient.

According to one embodiment, in response to a determination that the target anatomical structure of the patient includes an amount of cartilage that meets certain cartilage amount criteria for performing a surgery on the target anatomical structure of the patient, identifying the one or more points or regions as a recommended area for performing surgery.

According to one embodiment, identifying the one or more points or regions as a recommended area for performing surgery includes overlaying a visual indicator on an image of the target anatomical structure of the patient.

According to one embodiment, a certain cartilage amount criteria includes a criterion that is met when the thickness of the cartilage at the one or more points in the augmented patient-specific bone/cartilage model is less than a threshold amount of cartilage.

According to one embodiment, determining that one or more regions where the target anatomical structure of the patient includes an amount of cartilage that meets certain cartilage amount criteria for performing a surgery on the target anatomical structure of the patient includes determining at least one exposed portion of the target anatomical structure in the intraoperative patient-specific bone/cartilage data.

In addition, the disclosure relates to a computer program product comprising instructions which, when the program is executed by a computer, cause the computer to carry out the method for obtaining an augmented patient-specific bone/cartilage model a target anatomical structure of a patient described above.

The present disclosure further pertains to a computer-readable storage medium comprising instructions which, when executed by a computer, cause the computer to carry out the method for obtaining an augmented patient-specific bone/cartilage model of a target anatomical structure of a patient described above.

The present disclosure further pertains to a non-transitory program storage device, readable by a computer, tangibly embodying a program of instructions executable by the computer to perform a method for obtaining an augmented patient-specific bone/cartilage model of a target anatomical structure of a patient compliant with the present disclosure.

Such a non-transitory program storage device can be, without limitation, an electronic, magnetic, optical, electro-magnetic, infrared, or semiconductor device, or any suitable combination of the foregoing. It is to be appreciated that the following, while providing more specific examples, is merely an illustrative and not exhaustive listing as readily appreciated by one of ordinary skill in the art: a portable computer diskette, a hard disk, a ROM, an EPROM (Erasable Programmable ROM) or a Flash memory, a portable CD-ROM (Compact-Disc ROM).

Definitions

In the present invention, the following terms have the following meanings:

The terms "adapted" and "configured" are used in the present disclosure as broadly encompassing initial configuration, later adaptation or complementation of the present device, or any combination thereof alike, whether effected through material or software means (including firmware).

The term "processor" should not be construed to be restricted to hardware capable of executing software, and refers in a general way to a processing device, which can for example include a computer, a microprocessor, an integrated circuit, or a programmable logic device (PLD). The processor may also encompass one or more Graphics Processing Units (GPU), whether exploited for computer graphics and image processing or other functions. Additionally, the instructions and/or data enabling to perform associated and/or resulting functionalities may be stored on any processor-readable medium such as, e.g., an integrated circuit, a hard disk, a CD (Compact Disc), an optical disc such as a DVD (Digital Versatile Disc), a RAM (Random-Access Memory) or a ROM (Read-Only Memory). Instructions may be notably stored in hardware, software, firmware or in any combination thereof.

"Tridimensional (3D) model" refers to a three-dimensional digital (or virtual) model being a virtual object in 3 dimensions. The position and orientation of the model is known in the associated digital referential. The 3D model may be mathematically represented by a point cloud.

"Preoperative planning" in the context of surgery, refers to a list of actions to be performed during the different surgical phases. This surgical planning may be obtained by means of a simulation program carried out before the operation which uses a 3-dimensional digital model of the bone(s) of the patient that are the target of the surgery. In the case of a knee arthroplasty operation, for example, preoperative planning will consist of defining each of the cutting planes and drilling axes in relation to a three-dimensional model of the femur and tibia.

"Registration" refers to the computational process of aligning and overlaying multiple images, datasets, or geometric models to achieve spatial or structural correspondence so to facilitating analysis, comparison, or integration of visual data from different sources or at different time points. Key aspects of registration include the transformation of one or more data sets to match the spatial orientation, scale, and position of a common reference frame (i.e., referential). It may involve finding the optimal transformation parameters that minimize the disparity between corresponding features or points in the registered data. Registration techniques can vary from simple rigid transformations (translation, rotation, scaling) to more complex deformable transformations that account for non-rigid distortions.

"Target anatomical structure" refers to a distinct and identifiable part of a patient's body that requires surgery. In the context of the present invention, the target anatomical structure comprises bone tissues and cartilage tissues. In one example, the target anatomical structure does not comprise any other external objects such as a screw or a fiducial, but only human body parts. For example, the target anatomical structure may be the terminal portion of a tibia, including a tibia head covered by articular cartilage. Alternatively, the target anatomical structure may comprise any bone involved in a joint such as the knee joint, the elbow joint, the hip joint or the shoulder joint. For instance, the bone is the terminal portion of a talus, fibula, femur, pelvis, ulna, radius, humerus, scapula, clavicle and the surrounding cartilage. One objective of the present invention is to obtain a 3D patient-specific model of said target anatomical structure.

"Subject anatomical structure" refers to a distinct and identifiable part of a subject's body. In the present invention, the subject anatomical structure is the target anatomical structure in the subject. In other words, if the target anatomical structure is the terminal portion of a tibia, including the tibia head covered by articular cartilage, the subject anatomical structure is the corresponding terminal portion of a tibia, including the tibia head covered by articular cartilage of said subject. In the present invention, subject anatomical structures are captured on a plurality of subjects in order to construct a model representative of the variability of the target anatomical structure in a given population.

ILLUSTRATIVE EMBODIMENTS

The present description illustrates the principles of the present disclosure. It will thus be appreciated that those skilled in the art will be able to devise various arrangements that, although not explicitly described or shown herein, embody the principles of the disclosure and are included within its scope.

All examples and conditional language recited herein are intended for educational purposes to aid the reader in understanding the principles of the disclosure and the concepts contributed by the inventor to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein may represent conceptual views of illustrative circuitry embodying the principles of the disclosure. Similarly, it will be appreciated that any flow charts, flow diagrams, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, a single shared processor, or a plurality of individual processors, some of which may be shared.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces.

Figure 1:
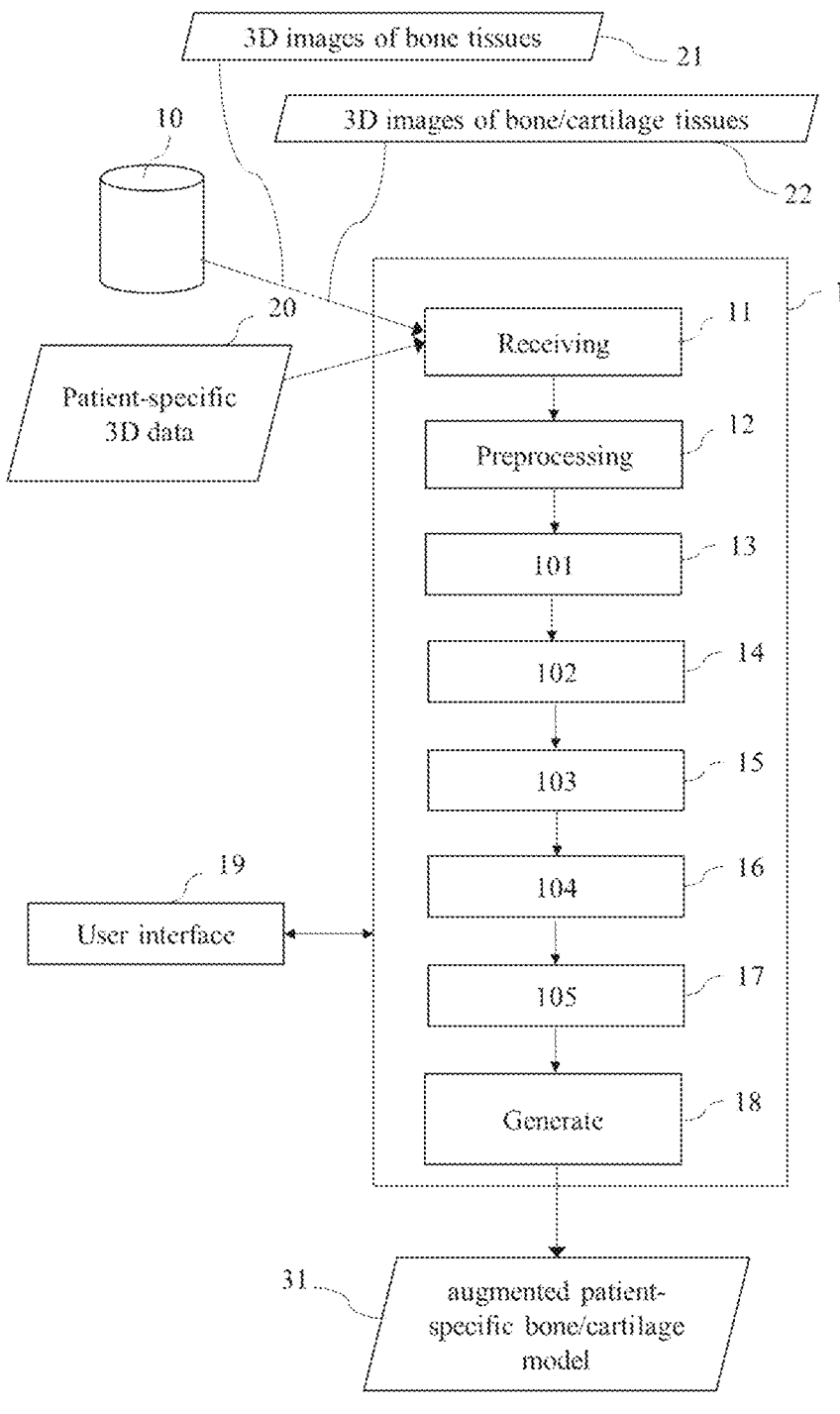
FIG. 1 is a block diagram representing schematically a particular mode of a device for obtaining an augmented patient-specific bone/cartilage model of a target anatomical structure of a patient, compliant with the present disclosure.

The present disclosure will be described in reference to a particular functional embodiment of a device 1 for obtaining an augmented patient-specific bone/cartilage model 31 of a target anatomical structure of a patient, as illustrated on FIG. 1.

Though the presently described device 1 is versatile and provided with several functions that can be carried out alternatively or in any cumulative way, other implementations within the scope of the present disclosure include devices having only parts of the present functionalities.

The device 1 is advantageously an apparatus, or a physical part of an apparatus, designed, configured and/or adapted to perform the mentioned functions and produce the mentioned effects or results. In alternative implementations, the device 1 is embodied as a set of apparatus or physical parts of apparatus, whether grouped in a same machine or in different, possibly remote, machines. The device 1 may have functions distributed over a cloud infrastructure and be available to users as a cloud-based service, or have remote functions accessible through an API.

In what follows, the modules are to be understood as functional entities rather than material, physically distinct, components. They can consequently be embodied either as grouped together in a same tangible and concrete component, or distributed into several such components. Also, each of these modules are possibly themselves shared between at least two physical components. In addition, the modules are implemented in hardware, software, firmware, or any mixed form thereof as well. They are preferably embodied within at least one processor of the device 1.

The device 1 comprises a module 11 for receiving the following input data: a dataset of 3D images acquired from a plurality of subjects and a previously generated patient-specific 3D model 20. All these input data may be stored in one or more local or remote database(s) 10. The latter can take the form of storage resources available from any kind of appropriate storage means, which can be notably a RAM or an EEPROM (Electrically-Erasable Programmable Read-Only Memory) such as a Flash memory, possibly within an SSD (Solid-State Disk).

The dataset of 3D images may have been obtained from a population of subjects that underwent a process of imaging the anatomical structure corresponding to the target anatomical structure. The obtained 3D images comprise at least part of the subject anatomical structure corresponding to the target anatomical structure that needs to be operated on. In other words, if a patient needs to have his knee operated on, the 3D images of the dataset are acquired on the knees of a plurality of subjects. In this database, several 3D images may correspond to a same subject (e.g. both knees of the subject may be imaged) or alternatively, each 3D image may be acquired on a different subject. Preferably, all the 3D images of the dataset comprise bone tissues of the subject anatomical structure and at least part of said 3D images comprise cartilage tissues of the subject anatomical structure.

According to a first example, the dataset only comprises 3D images acquired using an imaging technique that allows visualization of both bone tissues and cartilage tissues, such as 3D MRI images.

Alternatively, the dataset may comprise a first ensemble 21 of 3D images acquired using an imaging technique that allows visualization of bone tissues only, such as CT scanner images, and a second ensemble 22 of 3D images acquired using an imaging technique that allows visualization of both bone tissues and cartilage tissues, such as MRI imaging technique.

According to this example, these images from the first ensemble 21 and from the second ensemble 22 may be paired so that a 3D image of the first ensemble 21 captured on a given subject, has a corresponding 3D image, captured on the same subject, in the second ensemble 22. In other words, each subject may undergo both an imaging technique that allows visualization of bone tissues only and an imaging technique that allows visualization of both bone tissues and cartilage tissues to image his subject anatomical structure. A set of two paired 3D images may therefore be obtained for each subject, i.e., one 3D image for each dataset 21, 22. However, it has to be noticed that the method of the present invention may be implemented using only 3D images from the second ensemble 22 as both bone and cartilage are visible. In one example, the dataset comprises at least 3D images of the second ensemble 22.

In the exemplary case of Total Knee Arthroplasty (TKA), the subject anatomical structure represented in the 3D images of the first ensemble 21 is at least one portion of a femur or a tibia. More generally, the target anatomical structure can be any bone, such as a vertebra, a glenoid and the like, or articulation, such as a knee, a shoulder, an ankle and the like. The 3D images of the first ensemble 21 are therefore acquired with imaging techniques suitable to capture bones tissues. Notably, the 3D images of the first ensemble 21 may be obtained using X-ray images taken from different angles in order to obtain 3D images. Generally, acquisition of multiple 3D images is included in the clinical routine for patient that will undergo TKA surgery. In this case, an algorithm may be implemented to reconstruct a 3D image from the sparse 2D X-ray projections (e.g., EOS imaging). Alternatively, the 3D images of the first ensemble 21 may be obtained using Computer Tomography (CT) scans.

The 3D images of the second ensemble 22 comprise both visible bone tissues and visible cartilage from the target anatomical structure. Cartilage is a connective tissue that is positioned around bones in various parts of the body. It serves several important functions, including providing cushioning, reducing friction between bones, and aiding in joint movement. In the exemplary case of a TKA, the cartilage includes the articular cartilage that covers the ends of the femur and the tibia at the knee joint, and the patellar cartilage present on the undersurface of the kneecap that interfaces with the femur. The 3D images of the second ensemble 22 are therefore acquired with imaging techniques suitable to capture both bones and cartilage tissues. The 3D images of the first ensemble 21 may be obtained using Magnetic Resonance Imaging (MRI) techniques such as Proton Density-Weighted MRI, DESS (Double Echo Steady State) MRI or T2-Weighted MRI. Alternatively, the 3D images of the first ensemble 21 may be arthrograms obtained using Fluoroscopy-Guided Arthrography, MRI Arthrography, or CT Arthrography. It has to be noted that these medical imaging techniques are not commonly performed on patients that will undergo orthopedic surgery, due to the numerous contraindications for patients (e.g. excluded for patients with metallic implants or a pacemaker), the additional cost or lack of specific imaging technology required for the exams.

The patient-specific 3D model 20 may be directly received as an input by module 11 or it may be generated using 3D images of at least one portion of the target anatomical structure of the patient. The device 1 may be configured to receive the 3D images acquired on the patient that requires surgery. These 3D images are acquisition of the target anatomical structure of the patient, and they include at least one portion of the target bone. The 3D images of the patient may be acquired using CT-scanner or MRI as long as the bone structures are clearly visible. Device 1 may be in this case further configured to implement an algorithm for generating a patient-specific bone 3D model based on these 3D images. Any method known by the person skilled in the art may be used to generate the patient-specific bone 3D model, such as conventional segmentation neural networks.

Additionally, module 11 may be further configured to receive as an input at least one 3D image acquired from at least one 3D image sensor (i.e., an image representing a 3D object encompassing at least three spatial coordinates for each location of said image, e.g., a point cloud and/or depth map) during surgery. The at least one 3D image acquired from at least one 3D image sensor comprises at least one portion of the target anatomical structure, exposed during surgery, and may be a collection of discrete data points in 3D space, representing the external surface of the exposed portion of the target anatomical structure and, optionally, the rest of the surgical scene acquired. Each data point is defined by (x, y, z) coordinates, and optionally by additional properties.

The at least one 3D image sensor used to capture the at least one 3D image during surgery may be present in the surgical theater and positioned in such a way to comprise in its field of view at least a portion of the surgical field comprising the target anatomical structure. During orthopedic surgery, the surgeon proceeds to the exposure of the target anatomical structure, which in this case may be one or more bone(s), on which surgical operations, such as for example, machining or drilling have to be performed. The surgical field, which is basically the region of the patient on which the surgery is to be performed, will comprise the exposed target anatomical structure and the surrounding structures B such as tissues (i.e., cartilages, tendons, muscles, skin, or a bone which is not targeted during the surgery, and the like) and/or artificial structures (i.e., bone screw, surgical tools, grasping tools etc.).

In one embodiment, the 3D image sensor refers to a sensor for acquiring topological data of a real scene in 3 dimensions. These topological data are recorded in the form of a point cloud, and/or a depth map. Multiple acquisition techniques may be utilized to obtain these topological data for example techniques based on the measure of wave propagation time such as ultrasound or light (LIDAR, Time-of-Flight) or stereoscopic camera or sensor, which is a type of camera with two or more lenses with a separate image sensor or film frame for each lens. This allows the camera to simulate human binocular vision, and therefore gives it the ability to capture three-dimensional images. Other techniques may be based on light deformation, such as structured-light 3D scanners which project a pattern of light on an object and look at the deformation of the pattern on the object. The advantage of structured-light 3D scanners is speed and precision. Instead of scanning one point at a time, structured light scanners scan multiple points or the entire field of view at once. Scanning an entire field of view in a fraction of a second reduces or eliminates the problem of distortion from motion. Another class of techniques is based on laser scanning for sampling or scanning a surface using laser technology, such as hand-held laser or time-of-flight 3D laser scanner. More in general, any techniques known by the skilled artisan providing topological data of a real scene in 3 dimensions may be used for the implementation of the present invention. In one example, a probe is used to obtain this 3D image being topological data of the scene in 3 dimensions.

The 3D image(s) may be grayscale images, or colored depth (RGB-D) images among others. The 3D image(s) may include numerical data, such as digital data. Those data may include individual image data in a compressed form, as well known to a person skilled in image compression, such as e.g., in compliance with e.g., in compliance with JPEG (for Joint Photographic Experts Group), JPEG 2000 or HEIF (for High Efficiency Image File Format) standard.

According to one embodiment, the 3D sensor is a Cone Beam CT or a C-arm, or an ultrasound probe and the point clouds or topological data may be obtained by processing the 3D images derived from X-rays or ultrasound. Alternatively, the 3D sensor could include a tracked probe (e.g., tracked by an optical tracking device) to collect 3D points, or even a device capable of measuring cartilage thickness at specific locations.

Moreover, the module 11 may be further configured to receive as an input other information such as at least one distance or thickness measurement or estimation performed, on a predetermined position of the cartilage, during surgery or beforehand, or thickness estimation from imaging data (i.e., CT scan or MRI images of the patient, patient-specific data 20, etc.), or metadata associated to the patient such as the age, the sex, the Body Mass Index (BMI), the Hip-Knee-Ankle (HKA) angle, the arthrosis grade and/or data on the cartilage such as the thickness at a given position. For instance, such distance may be the interosseous distance between the bones in an articulation (for example, the distance between the femur and the tibia). It may provide information on the maximum size of the cartilage, which is restricted by this interosseous distance.

Module 12 may be optionally configured to perform a preprocessing of the 3D images from the first ensemble 21 and the second ensemble 22.

Preprocessing of the 3D images may include preprocessing to improve segmentation performed on the 3D images. For instance, the 3D images may undergo various image processing techniques such as data augmentation (translation/rotation, blur, contrast modification, addition of noise), the use of a threshold (often employed for segmenting CT and/or MRI images, given that different tissues do not have the same "color" of pixels). Other types of preprocessing may be performed on the 3D images, such as contrast adjustment, Hounsfield Unit threshold adjustment, smoothing, filtering, down sampling or resampling.

Post-processing may also be performed by module 12 on the segmented meshes, such as wrapping (hole filling), smoothing or decimation.

The device 1 may also include a module 13 configured to segment 101 the bone tissues in each 3D image of at least two 3D images of the dataset. In one example, two or more 3D images of the first ensemble 21 are processed to segment bone tissues. The segmentation step comprises obtaining a 3D mesh of the bone tissues for each 3D image of the first ensemble 21. Conventional segmentation algorithms based on CNN such as U-net or 3D U-net may be used for segmentation. Any other suitable automated algorithm known by the person skilled in the art may be used for the segmentation of the bone tissues and the cartilage tissues in each 3D image. In one alternative embodiment, the segmentation may be performed manual delineation by a user.

The device 1 may further include a module 14 configured to determine 102 a bone Statistical Shape Model (SSM)

based on the multiples segmented portions bone tissues obtained from the 3D images of the first ensemble 21.

The statistical shape model (SSM) advantageously allows to describe the variation of the anatomy of the bone tissues in a population by conventional multivariate statistics of dense sets of homologous landmarks representing the shape of the underlying structures. Statistical shape modeling provides a powerful tool for describing the bone anatomy. By linearly combining the variance of the shape of the subjects of the first ensemble 21, statistical shape models (SSMs) identify its main modes of variation and may approximate the total variance of that population of subjects to a selected threshold, while reducing its dimensionality.

In other words, the SSM provides a representation of the average shape and the characteristic variations in shape. The SSM may be represented by a vector x that comprises a set of selected 3D landmarks distributed on the surface of the bone tissues, $\bar{x}$ represents the mean shape and Pb are the variations, wherein P comprises the variation components or modes and b is a vector of scaling values for each variation component.

$$x \approx \bar{x} + Pb$$

In the present invention, to obtain the bone SSM, the segmented 3D meshes of bone tissues obtained for each 3D image of the first ensemble 21 are aligned in order to find corresponding points between the aligned 3D meshes. To that end, a first rigid registration may be performed to coarsely align the segmented 3D meshes and then a non-rigid registration may be performed to find the corresponding points. In one example, ICP (Iterative Closest Point) or generalized ICP, or Procrustes Analysis, may be used to perform the rigid registration while CPD (Coherent Point Drift) algorithm or B-splines registration are implemented to perform non-rigid registration. A Principal Component Analysis may then be performed on the matching points to obtain the modes P and the scaling values b (i.e., to extract the principal components of shape variation). Alternatively, any other method suitable for generating a statistical shape model which is known by the person skilled in the art may be implemented (e.g., Procrustes analysis, deep learning approaches such as CNN or autoencoder, etc.).

According to one embodiment, the bone SSM obtained by module 14 is augmented with landmarks of anatomical or clinical relevance. These landmarks, if annotated (manually or automatically) on a set of patients, may be transferred from the patients to the SSM fitted shape and generalized on the overall SSM mean shape, learning a SSM augmented with landmarks. These landmarks may later be transferred from the augmented SSM onto new patients. One example of relevant clinical landmarks is the exposed area during TKA surgery, where the annotation may be the point clouds of intraoperative scenes captured by a 3D imaging sensor (e.g., RGBD sensor), registered onto the patient-specific 3D model 20. This may also be extended to the bone and cartilage SSM (i.e., global Statistical Shape Model), that will be discussed in detail in the following embodiments.

The device 1 also comprises a module 15 configured to perform step 103 of obtaining a global dataset comprising the optimized bone Statistical Shape Model. Notably, step 103 first comprises segmenting the subject anatomical structure in each 3D image of at least two 3D images of the dataset comprising cartilage tissues of the subject anatomical structure. In one example, the segmentation is performed on two or more 3D images of the second ensemble 22. In other words, the module 15 is configured to segment both the bone tissues and the cartilage tissues in each 3D images. Conventional segmentation algorithms based on CNN, such as U-net or 3D U-net, may be used for segmentation. The same type of segmentation algorithm than the one used to segment the bone may be used and optionally retrained on another type of 3D image and to identify also the cartilage tissues. Any other suitable automated algorithm known by the person skilled in the art may be used for the segmentation of the bone tissues and the cartilage tissues in each 3D images. In one alternative embodiment, the segmentation may be performed manual delineation by a user.

The segmentation step of step 103 allows to obtain, for each 3D image of the second ensemble 22, a 3D mesh of the bone tissues and a 3D mesh of the cartilage tissues. The 3D mesh of the bone tissues is therefore positioned relative to the 3D mesh of the cartilage tissues so that the distance between the points belonging to the bone tissues and the points belonging to the cartilage tissues is known.

Module 15 is further configured to perform a rigid registration of the bone SSM, obtained using module 14, with the bone tissues segmented from each 3D image of the second ensemble 22. In other words, the bone SSM and the 3D mesh of the bone tissues obtained from each 3D image of the second ensemble 22 are aligned through rigid registration. This feature enables fitting the bone Statistical Shape Model (SSM) to 3D meshes. Notably, the combination of rigid registration and SSM fitting (i.e., optimizing the weights in the formula $\bar{x}+Pb$) avoids the need for non-rigid registration, which could excessively deform the bone SSM to match the patient data. By maintaining the structural integrity of the SSM, this approach ensures a more anatomically consistent and reliable fit, which is particularly advantageous for applications requiring precise and realistic modeling of patient-specific anatomy. The combination of rigid registration and SSM optimization enables matching the bone SSM to 3D meshes, thereby establishing correspondences on the bone for each patient. Additionally, since this approach provides a smoother approximation of the 3D meshes compared to standard segmentation methods, it facilitates more precise and consistent correspondences on the cartilage. This dual benefit enhances the overall accuracy and reliability of patient-specific modeling, offering significant advantages for applications that require detailed and anatomically faithful representations of bone and cartilage structures.

The scaling values b of the bone SSM are then optimized to make the bone SSM correspond with the bone tissues obtained from each 3D image of the second ensemble 22. The steps of rigid registrations and optimizations may be performed one after the other or simultaneously on each 3D mesh without changing the invention. According to one embodiment of the invention, the optimization of the parameters is achieved by minimizing a cost function.

Module 15 is further configured to obtain a global dataset comprising the optimized bone Statistical Shape Model associated with the cartilage tissues from the segmented subject anatomical structure. The global dataset may then be defined as comprising a pair of information for each 3D image of the second ensemble 22 (i.e., for each subject). Each pair of information, associated to the $i^{th}$ 3D image of the second ensemble 22, comprises the optimized bone SSM (i.e., optimized to match the 3D mesh of the bone of the $i^{th}$ 3D image) and the associated segmented cartilage tissues, co-registered in a common referential. In other words, each optimized bone SSM is associated with the corresponding 3D mesh of the cartilage tissues obtained thanks to the second ensemble 22. Because the distance between the points belonging to the bone tissues and the points belonging to the cartilage tissues where previously known, it is possible to deduce the distance between the optimized bone SSM and the cartilage tissues for each segmented cartilage.

Module 16 of the device 1 may be configured to perform step 104 of determining a global Statistical Shape Model (SSM) representative of both the bone tissues and the cartilage tissues of the subject anatomical structures based on said global dataset. Said global Statistical Shape Model advantageously includes a bone portion corresponding with said segmented bone tissues of the subject anatomical structure, and a cartilage portion corresponding with cartilage tissues from said segmented subject anatomical structure, therefore each of the bone portion and the cartilage portion being represented by a Statistical Shape Model. In other words, the global SSM is constructed so as to represent the average shape and the characteristic variations in shape of both the bone tissues and the cartilage tissues in the population of the first ensemble 21 and second ensemble 22. Advantageously, having a unified SSM yields a more accurate representation of the patient's anatomy, as the global Statistical Shape Model in the invention has been trained to learn both the shapes of the cartilage and bone concurrently, capturing their interdependencies. Thus, a more accurate modelling of a patient-specific bone/cartilage is obtained.

In order to obtain the global SSM, the module 16 is configured to, for each 3D mesh of cartilage tissue from the global dataset, generate a plurality of vectors normal to the surface of the optimized bone SSM so that said vectors intersect the 3D mesh of the cartilage tissues. The associated optimized bone SSM is used to identify a grid of points on the corresponding 3D mesh of cartilage tissues from which the generated normal vectors pass through, said grid of points being therefore reproduceable from one 3D mesh of the cartilage tissues to another. In general, two intersection points are obtained for each normal vector: a point belonging to the internal surface of the cartilage (entry point) and one point belonging to the external surface of the cartilage (exit point). In case of zero cartilage thickness, the two points coincide. Multiple ensembles of intersection points are obtained, one for each 3D cartilage mesh (i.e., subject) of the global dataset. A PCA may then be performed on these ensembles of intersection points to obtain the modes P and the scaling values b of the cartilage part of the global SSM. As explained before, any other method for construction known by the person skilled in the art may be used to construct the global SSM.

The device 1 further comprises a module 17 configured to perform 105 a rigid registration between the bone portion of the global SSM and the patient-specific 3D model 20 received as an input by module 11.

The scaling values b of the global SSM may be then optimized to make the global SSM correspond with the target bone from the patient-specific 3D data. The steps of rigid registration and optimization may be performed one after the other or simultaneously without changing the invention. According to one embodiment of the invention, the optimization of the parameters is achieved by minimizing a cost function.

Advantageously, the optimization of the global SSM may be improved thanks to the received at least one thickness measurement performed on a predetermined position of the cartilage (i.e., measure obtained during the surgery). In the same manner, the optimization may also be improved with the at least one metadata received as an input by the device 1. The thickness measurement and/or the metadata may be used to constrain the optimization of the global SSM. Constraining the optimization with additional data improves its anatomical plausibility, stability, and interpretability while reducing overfitting.

The device 1 further comprises a module 18 configured to generate the augmented patient-specific bone/cartilage model of the target anatomical structure based on the optimized global SSM registered with the patient-specific 3D data.

The augmented patient-specific bone/cartilage model may be generated before surgery. In this case, an STL/PLY file with a fixed cartilage mesh is obtained.

According to one embodiment, device 1 further comprises a module configured to post-process the bone part of the augmented patient-specific bone/cartilage model 31 in the case of cartilage prediction from bone. Once the augmented patient-specific bone/cartilage model is generated and the cartilage is predicted, it is advantageous for the user to keep only the cartilage prediction and replace the bone part of the overall model by the bone segmentation which often more precisely fits to the patient bone anatomy depicted in the imaging modality (from first ensemble 21 or second ensemble 22). However, the segmented bone model may cross/intersect with the predicted cartilage surface (for example in the case of osteophytes). In this case several methods may be used. In one example, the bone part of the augmented bone/cartilage model is directly replaced by the segmented bone as they are in the same reference frame due to the bone fitting step, then the eventual crossings are handled by computing the intersection of the normals of the segmented bone model with the cartilage part of the augmented bone/cartilage model, and finally the segmented bone model vertices is replaced by the intersection with the predicted cartilage. In case of no intersection, the segmented bone surface is outside of the cartilage and thus corresponds either to a case of bone/cartilage crossing or a point outside the subchondral area where there is no cartilage that covers the bone (for example the diaphysis). In one example, the module is configured to project normals from the bone mesh. When these normals intersect cartilage, it indicates the presence of cartilage overlying the bone, and to construct the global bone and cartilage SSM model, where the corresponding cartilage point replaces the bone point. If the normals do not intersect any structure, two possible scenarios arise. The first scenario occurs outside the subchondral zone, such as in the diaphysis and certain regions of the epiphysis, where no cartilage is naturally present. In these areas, no intersection with cartilage is detected due to its natural absence. The second scenario occurs within the subchondral bone zone, where the absence of intersection may result from the presence of osteophytes. These bony outgrowths can extend beyond the cartilage layer, effectively "penetrating" the cartilage zone.

In another example a non-rigid registration of the bone part of the augmented bone/cartilage model onto the segmented bone model is performed.

Advantageously, such complete and accurate patient-specific bone/cartilage model 31 may be used to improve precision of guidance of a cobot for orthopedic surgery. In the context of fiducial-less orthopedic surgery, such as presented in patent application PCT/EP2020/061522, a 3D model of the anatomical structure of the patient may be used to find a transformation allowing to transfer the planned surgical actions into the reality of the surgical theater (by co-registering the 3D model and a 3D depth image of the exposed anatomical structure to threat). In this case scenario, the correct positioning of the cobot directly depends from the precision of registration between the patient-specific 3D model of the anatomical structure and its (intraoperative) 3D image, and the precision of registration is all the more accurate if the patient-specific 3D model reproduces as faithfully as possible the reality of the target structure represented in said 3D depth image. The surgeons usually do not remove the cartilage during the surgery (i.e., the 3D image comprises cartilage tissues), therefore the present patient-specific 3D model, representing both bone and cartilage, strongly improves registration precision.

The device 1 may optionally include an intra-operative module configured to register the at least one exposed portion of the target anatomical structure from the at least one 3D image, captured during surgery and received as an input by module 11, with the augmented patient-specific bone/cartilage model 31.

More precisely, the at least one 3D image captured during surgery may be in the form of a cloud point. The bone and cartilage modelized in the patient-specific bone/cartilage model are aligned with the points belonging to the exposed bone and cartilage from the 3D images captured during surgery. The intra-operative module is further configured to optimize at least one parameter of the augmented patient-specific bone/cartilage model 31. The steps of registration and optimization may be performed one after the other or simultaneously without changing the invention. According to one embodiment of the invention, the optimization of the parameters is achieved by minimizing a cost function.

To optimize the augmented patient-specific bone/cartilage model with the target anatomical structure of the patient exposed during surgery, an initial optimization of the global SSM is performed, which gives a first estimation of the cartilage part/portion of the global SSM. This information is stored in the format of an optimal vector rather than an STL/PLY cartilage mesh. Then, this vector is used for the initialization of the intraoperative registration. In this case, the cartilage part is deformable, while the bone part is fixed and the augmented patient-specific bone/cartilage model may be optimized by adapting the shape of the cartilage in the augmented patient-specific bone/cartilage model.

Moreover, additional intraoperative information can be used to refine the augmented patient-specific bone/cartilage model 31 during the registration process. For example, it is possible to use the outcome of a module that automatically detects the areas without cartilage in RGB images or RGB-D images captured during surgery.

In examples in which the device 1 includes an intra-operative module, said intra-operative modules may be configured to continuously or regularly (i.e., with a certain frequency) register said at least one exposed portion from the at least one 3D image, captured during surgery with the augmented patient-specific bone/cartilage model 31. Said images are continuously or regularly received as an input by module 11. In other words, these examples update the augmented patient-specific bone/cartilage model 31 in the course of the surgery. This provides a consistently accurate model throughout the surgery process.

Alternatively or in addition, the device 1 may communicate via a network or wi-fi the augmented patient-specific bone/cartilage model 31 to a device for the computer guided surgery, such as the one of patent application PCT/EP2020/061522, to be used as digital model of the target.

Advantageously, the augmented patient-specific bone/cartilage model 31 may be used in a device for designing a patient-specific implant or choosing an appropriate implant in a list of implants with different features.

Alternatively, the augmented patient-specific bone/cartilage model 31 may be used to predict the evolution of a disease such as arthrosis, arthritis, osteoporosis, osteonecrosis and the like. Indeed, the augmented patient-specific bone/cartilage model 31 relies on statistical data that may allow for accurate prediction.

The device 1 may interact with a user interface 19, via which information can be entered and retrieved by a user. The user interface 19 includes any means appropriate for entering or retrieving data, information or instructions, notably visual, tactile and/or audio capacities that can encompass any or several of the following means as well known by a person skilled in the art: a screen, a keyboard, a trackball, a touchpad, a touchscreen, a loudspeaker, a voice recognition system.

Figure 2:
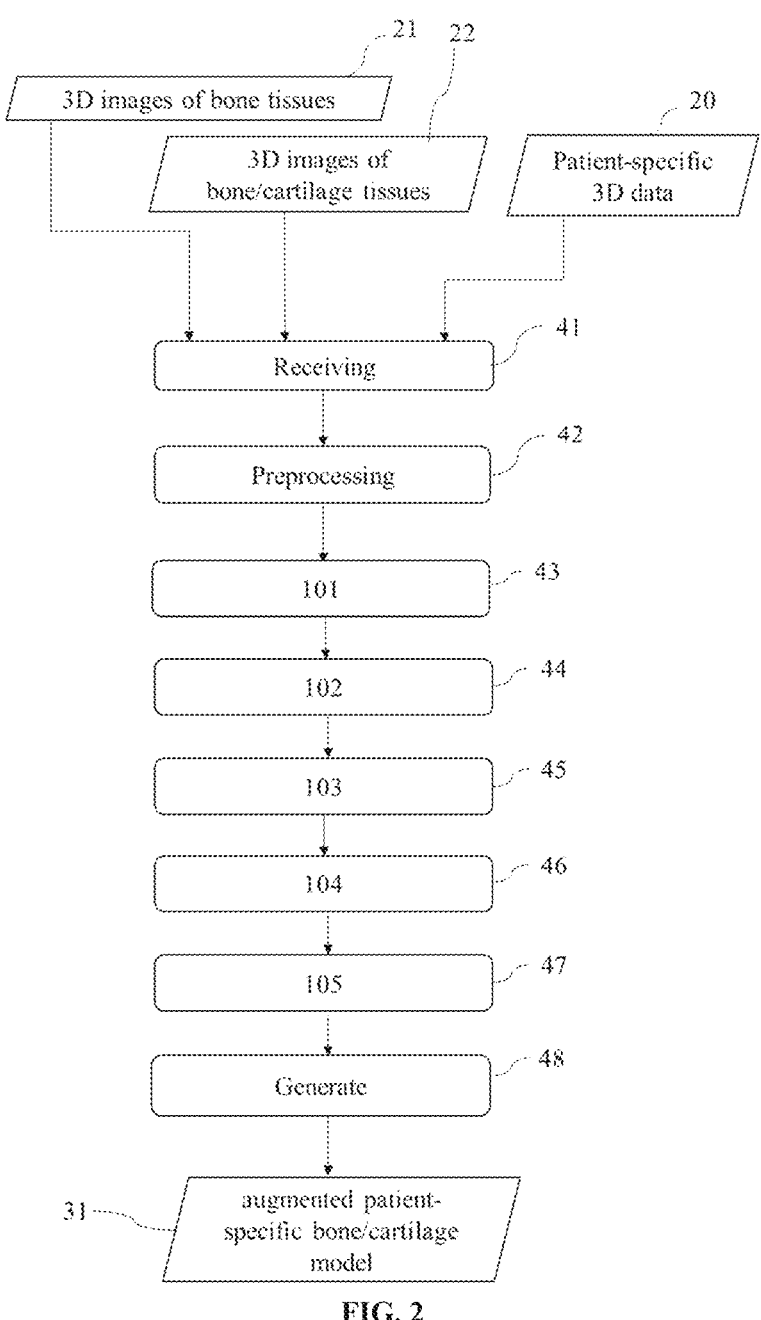
FIG. 2 is a is a flow chart showing successive steps executed with the device for obtaining an augmented patient-specific bone/cartilage model of a target anatomical structure of a patient of FIG. 1.

In its automatic actions, the device 1 may for example execute the following process illustrated on FIG. 2:

receiving a dataset comprising a first ensemble comprising 3D images acquired from a plurality of subjects, wherein bone tissues from the target anatomical structure are visible, the second ensemble comprising 3D images acquired from a plurality of subjects, wherein bone tissues and cartilage tissues from the target anatomical structure are visible and the previously acquired patient-specific 3D data of at least one portion of said target bone of the patient (step 41), optionally, preprocessing the 3D images included in the first ensemble, second ensemble and patient-specific 3D data (step 42), segmenting the at least one portion of the target bone in each 3D image of the first ensemble (step 43), determining the bone SSM based on the segmented portions of target bones obtained from the first ensemble (step 44), segmenting the target anatomical structure in each 3D image of the first ensemble and performing a rigid registration of the bone SSM with at least one portion of the segmented anatomical structure corresponding to the at least one portion of target bone and optimizing at least one parameter of the bone SSM to correspond with said at least one portion of target bone so as to obtain a global dataset comprising the optimized bone SSM associated with the segmented cartilage from the segmented target anatomical structure (step 45), determining a global SSM of the at least one portion of target bone and target cartilage of the target anatomical structure based on the global dataset (step 46), performing a rigid registration of the at least one portion of target bone from the global SSM with the patient-specific 3D data and optimizing at least one parameter of said global Statistical Shape Model to correspond with said patient-specific 3D data (step 47), generating said augmented patient-specific bone/cartilage model of the target anatomical structure based on the optimized global Statistical Shape Model registered with said patient-specific 3D data 20 (step 48).

Additionally, the device 1 may for example execute a step of localization of the target anatomical structure intraoperatively.

Figure 3:
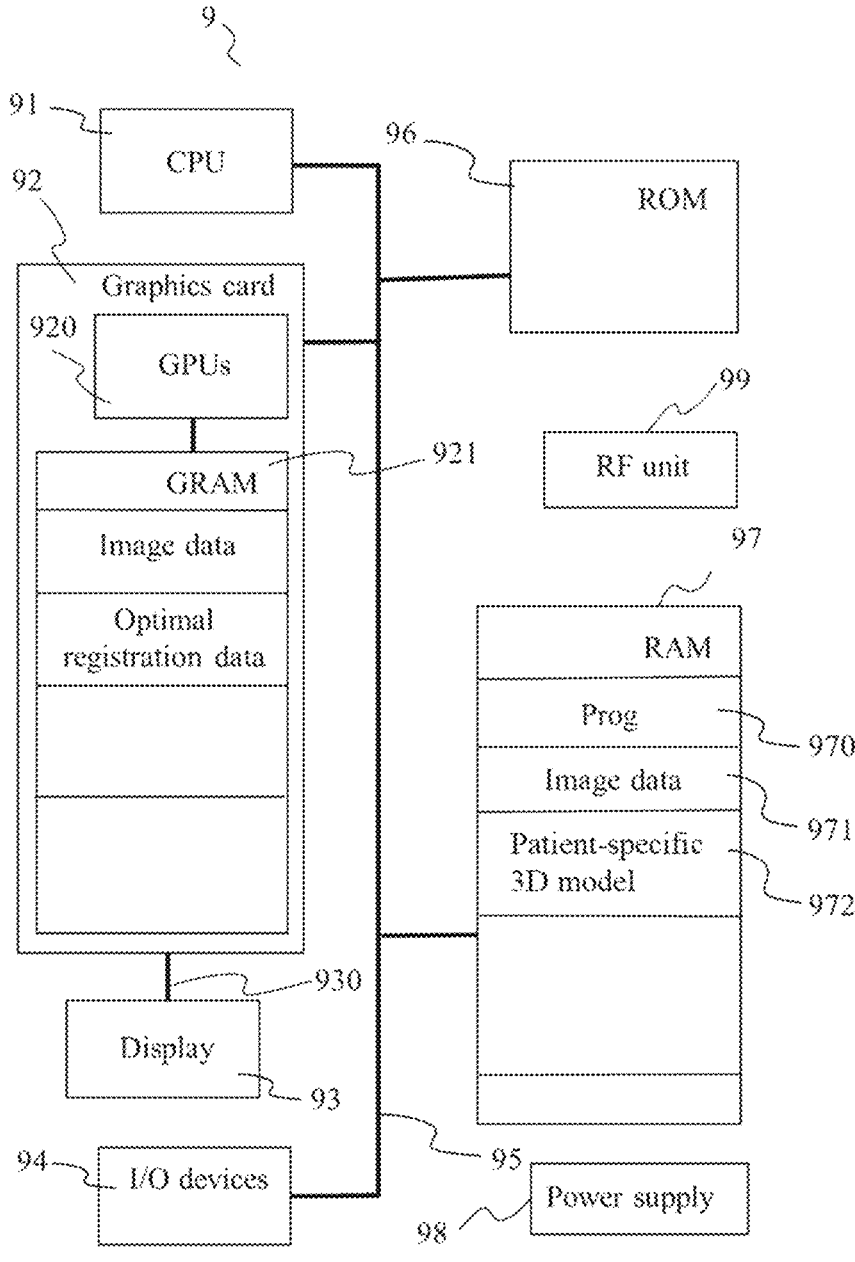
FIG. 3 illustrates an apparatus embodying a device for obtaining an augmented patient-specific bone/cartilage model compliant with the present disclosure, such as the device of FIG. 1.

A particular apparatus 9, visible on FIG. 3, is embodying the device 1 described above. It corresponds for example to a workstation, a laptop, a tablet, a smartphone, or a head-mounted display (HMD).

That apparatus 9 is suited for segmentation of 3D images and registration of a model of an exposed target anatomical structure on the 3D images. It comprises the following elements, connected to each other by a bus 95 of addresses and data that also transports a clock signal;

a microprocessor 91 (or CPU);

a graphics card 92 comprising several Graphical Processing Units (or GPUs) 920 and a Graphical Random Access Memory (GRAM) 921; the GPUs are quite suited to image processing, due to their highly parallel structure;

a non-volatile memory of ROM type 96;

a RAM 97;

one or several I/O (Input/Output) devices 94 such as for example a keyboard, a mouse, a trackball, a webcam; other modes for introduction of commands such as for example vocal recognition are also possible;

a power source 98; and a radiofrequency unit 99.

According to a variant, the power supply 98 is external to the apparatus 9.

The apparatus 9 also comprises a display device 93 of display screen type directly connected to the graphics card 92 to display synthesized images calculated and composed in the graphics card. The use of a dedicated bus to connect the display device 93 to the graphics card 92 offers the advantage of having much greater data transmission bitrates and thus reducing the latency time for the displaying of images composed by the graphics card. According to a variant, a display device is external to apparatus 9 and is connected thereto by a cable or wirelessly for transmitting the display signals. The apparatus 9, for example through the graphics card 92, comprises an interface for transmission or connection adapted to transmit a display signal to an external display means such as for example an LCD or plasma screen or a video-projector. In this respect, the RF unit 99 can be used for wireless transmissions.

It is noted that the word "register" used hereinafter in the description of memories 97 and 921 can designate in each of the memories mentioned, a memory zone of low capacity (some binary data) as well as a memory zone of large capacity (enabling a whole program to be stored or all or part of the data representative of data calculated or to be displayed such as image data 971 or the patient-specific 3D model 972). Also, the registers represented for the RAM 97 and the GRAM 921 can be arranged and constituted in any manner, and each of them does not necessarily correspond to adjacent memory locations and can be distributed otherwise (which covers notably the situation in which one register includes several smaller registers).

When switched-on, the microprocessor 91 loads and executes the instructions of the program 970 contained in the RAM 97.

As will be understood by a skilled person, the presence of the graphics card 92 is not mandatory and can be replaced with entire CPU processing and/or simpler visualization implementations.

In variant modes, the apparatus 9 may include only the functionalities of the device 1. In addition, the device 1 may be implemented differently than a standalone software, and an apparatus or set of apparatus comprising only parts of the apparatus 9 may be exploited through an API call or via a cloud interface.

EXAMPLE

1. Materials and Methods 1.1. Dataset the publicly available OAI-ZIB dataset is used, which consists of 507 manual segmentations of femoral and tibial bone and cartilage carried out by experienced users of the Zuse Institute Berlin. Segmentations were performed on 3D DESS (double-echo steady state) MRIs of the knee from the Osteoarthritis Initiative database (https://nda.nih.gov/oai), with an image resolution of 0.36×0.36×0.7 mm. The dataset includes patients with a relatively even split between men and women, a mean age of 61.87 years, a mean BMI score of 29.27 kg/m2, and with all knee osteoarthritis (KOA) grades being depicted. In order to study the impact of KOA on SSM cartilage prediction, models were trained on patients with different pathology levels. As explained, KOA is characterized by osteophytes and by reduced cartilage thickness and joint space width. It can be assessed by several grading systems, the most used being the Kellgren-Lawrence (KL) score based on 2D X-rays. However, it combines joint space narrowing (JSN) and osteophytes in a global score which wrongly assumes that these features occur continuously. On the contrary, the OA Research Society International (OARSI) atlas system splits these radiographic features in separate semi-quantitative scores, even dividing JSN into medial and lateral compartment features. As osteophytes are not highly sensitive indicators of cartilage wear, it was chosen to differentiate patients' KOA grade based on JSN and train models to capture the cartilage thickness variability between healthy and pathological patients. Based on the clinical assessments from the OAI database, the patients were divided according to the "evidence of knee lateral/medial joint space narrowing" criteria computed from the knee baseline X-ray, regardless of the evidence of osteophytes. A JSN degree of 0, 1 or 2—corresponding to normal, narrowed or severe JSN—was given to each patient for both lateral and medial sides. Patients were finally grouped in four different subdatasets (Table 1): patients with a medial, lateral or bilateral JSN and cartilage loss, and patients with premorbid JSN and cartilage thickness, considered healthy in this example regardless of their degree of osteophytes.

TABLE 1

Dataset grouping based on the JSN degree (format: medial-lateral)

|  | | Grouping | | |
| --- | --- | --- | --- | --- |
|  | Healthy | Lateral KOA | Bilateral KOA | Medial KOA |
| JSN degree (medial-lateral) | 0-0 | 0-1, 0-2, 1-2 | 1-1, 2-2 | 2-1, 2-0, 1-0 |
| Number of patients | 162 | 88 | 23 | 234 |
| Train/test set distribution | 129/33 | / | / | 187/47 |

TABLE 2

Dataset distribution and grouping based on the JSN degree (format: medial-lateral)

| JSN degree | 0-0 | 0-1 | 0-2 | 1-2 | 1-1 | 2-2 | 2-1 | 2-0 | 1-0 |
| --- | --- | --- | --- | --- | --- | --- | --- | --- | --- |
| Number of patients | 162 | 39 | 47 | 2 | 22 | 1 | 7 | 101 | 126 |
| Grouping | Healthy: 162 | Lateral KOA: 88 | | | Bilateral KOA: 23 | | Medial KOA: 234 | | |

In this example, it is focused on the groups corresponding to patients with premorbid and medial JSN, in order to have sufficient data to train a SSM. They will be referred to as healthy and pathological sets in the next sections. Each dataset was divided into training and testing sets with a 80/20% ratio (see table 1), leading to 102/24 patients of grade 1 (1-0) and 85/23 of grade 2 (2-1 and 2-0) in the pathological train and test sets respectively. Once the train and test sets were computed, the degree of osteophytes was assessed as the "evidence of knee osteophytes" criteria from the right knee baseline X-ray, again obtained from the clinical assessments of the OAI database. Distribution among the healthy and pathological train and test sets is presented in table 3. It shows that patients considered healthy in terms of JSN in this study can have various osteophytes' grades, even severe. It also shows that patients considered pathological tend to have a higher osteophytes grade, although a few don't have any.

TABLE 3

Osteophytes' distribution among healthy and pathological train and test sets 1.2. Statistical shape model

|  | Osteophytes' grade | | |
| --- | --- | --- | --- |
|  | 0 (none) | 1 (possible, minute) | 2 (definite, OARSI grade 1-3) |
| Healthy train set | 49 | 37 | 43 |
| Healthy test set | 11 | 4 | 18 |
| Pathological train set | 5 | 18 | 164 |
| Pathological test set | 1 | 4 | 42 |

To compute a coupled SSM that encompasses bone and cartilage, bone and cartilage point clouds with vertices ordered in correspondence are needed to be obtained, meaning that they represent the same physical anatomical location or feature, for all patients of the training set. A bone SSM was trained on the bones from the training set in order to first obtain the correspondences on the bone part of each patient mesh. To do so, one of the bone meshes was randomly selected as a template shape. A pre-alignment was performed to roughly place all bones' distal area in the template reference frame and deal with the differences in scaling and diaphysis' length throughout the database. Rigid registration was performed by successively applying an Iterative Closest Point (ICP) algorithm between each training bone and the template mesh, then computing a new template as the mean of all training meshes. Convergence is reached when the template shape's changes between iterations falls below a defined threshold. The template mesh was then non-rigidly registered on each training shape using recursive B-splines registration of the elastix toolbox on computed distance maps. This allowed to compute the correspondences. Modes of variations were finally extracted from corresponding bones using a Principal Component Analysis (PCA). From the bone SSMs, it is possible to generate new bone instances y as a linear combination of the mean shape and of the weighted modes of variation: $y=\bar{x}+Pb$ (equation 1) with $\bar{x}$ the mean of the aligned training shapes, P the eigenvectors of the covariance matrix computed during the PCA which represent the principal components of variation, and b a vector of weights. P can be truncated to select only the first modes, which are the most significant ones. The number of modes is usually chosen as to explain 95% of the total variance of the population. In order to restrict the generated outputs to plausible shapes, b can be bounded within the range $[-3\sqrt{\lambda_i}, 3\sqrt{\lambda_i}]$ for $i\in[1, \ldots, M]$, with M the number of modes used and $\lambda_i$ the eigenvalues corresponding to the ith eigenvector. Then the optimal weights in equation 1 can be found to generate an instance that best fits to a target shape, which can be partial data in the case of inference. By fitting the bone SSM to the bone meshes of the training set, it is possible to generate new shapes close to the original ones. In addition, the vertices of these approximated shapes are now all indexed with the correspondences established in the bone SSM, which allows for a dataset of corresponding bones. The next step is to compute the correspondences on the cartilage part of the training shapes. First, the indices of the bone vertices that correspond to the subchondral area need to be computed, i.e. located beneath cartilage. This is achieved by computing the union for all patients of the nearest neighbors of the cartilage mesh's vertices on the corresponding bone point cloud. Then the normals of the bone Mesh are used, starting from the subchondral points, to intersect the cartilage mesh. The two intersected points correspond to the internal and external faces of the cartilage mesh, except in the case where there is no cartilage thus no intersection point (for example holes in the cartilage, or reduced subchondral area). By indexing, for each subchondral point of all training shape, the two intersection points—or twice the subchondral point in case of no cartilage—, corresponding cartilage point clouds are obtained. For each patient, it is possible to merge the bone and cartilage corresponding point clouds. Since all patients' global bone and cartilage point clouds are now corresponding, a Procrustes Analysis can be used to align them in a same reference frame. Mean shape is computed and PCA applied to extract the modes of variation in order to generate a coupled SSM encompassing bone and cartilage. Equation 1 applies the same for both fitting and inference. Four coupled SSMs were generated: for femur and tibia, for both healthy and medial pathology training sets for each. Finally, it is possible to infer the cartilage shape of a new patient whose cartilage is unknown by fitting the bone part of the coupled SSM to the patient bone model. The cartilaginous part of the coupled SSM follows the same deformation and is thus well adapted to the patient.

1.3. Evaluation

The coupled SSM was first evaluated using metrics, which assess the quality of the correspondences established during the SSM generation. Compactness describes the model's ability to represent shape variation within a minimal number of modes and is quantified by the cumulative variance value. Generalization is the ability to represent unseen shapes: several SSMs are built from the training set where one shape was excluded, and then fitted to that shape. The fitting result is then compared to the excluded shape using root mean square error (RMSE). In this example, 10 leave-one-outs were performed to compute the overall generalization error. Specificity is the capacity to generate instances similar to what the model learnt in the training set.

A large number of random shapes (here, 10 000) is generated (by sampling from the distribution of modes) and compared to the training shapes in terms of RMSE. Cartilage thickness for both healthy and pathological train sets was computed from the normals' method, used in the cartilage correspondences establishment (2.2). For each patient of the training set, a thickness value was affected to each vertex of the subchondral part of the SSM fitted bone, computed as the Euclidean distance between the two intersections of the cartilage mesh. Then, mean and standard deviation values were computed for each vertex and projected on the mean SSM bone as color maps. The coupled SSM's capacity to fit to a new bone shape and predict cartilage distribution was assessed. Several error metrics were computed on the test sets and summarized by the median and 95th percentile values, to avoid taking potential outliers into account. The bone fitting error was first computed as the point-to-surface distance between the fitted SSM bone point cloud and the patient bone mesh. Cartilage prediction from the coupled SSM was also assessed, as the point-to-surface distance between the predicted cartilage point cloud and the bone and cartilage original mesh from the segmentation. For the error maps, the median and 95th percentile values were computed for each vertex over all patients. For the boxplots, the median error was rather computed on the overall shape for each patient of the test set. Finally, for each patient of the test set, the cartilage was also predicted by the non-corresponding model, i.e. the healthy coupled SSM was fitted to patients with medial pathology and vice versa. It allows to assess the match between the training data and the resulting model, and whether having two distinct models improves prediction.

2. Results 2.1. SSM validation: SSM validation metrics are presented in FIG. 4, with error bars corresponding to the standard errors in the case of generalization and specificity. The dotted lines on the compactness plots indicate the number of modes needed to explain 95% of variance: 65 and 70 for healthy femur and tibia models, 87 and 89 for pathological ones. This shows that more modes are necessary to explain a same amount of variability in pathological models and, to a lesser extent, in tibial models as compared to femur ones.

Figure 5:
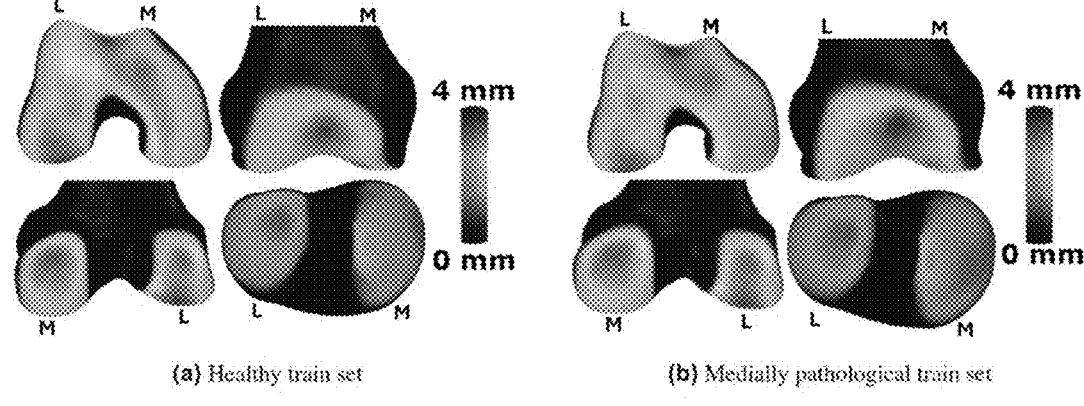
FIG. 5 represents mean cartilage thickness maps, for healthy and pathological patients of the train set. Lateral and medial sides are indicated by the letter L and M; (a) healthy train set (b) medially pathological train set.
Figure 6:
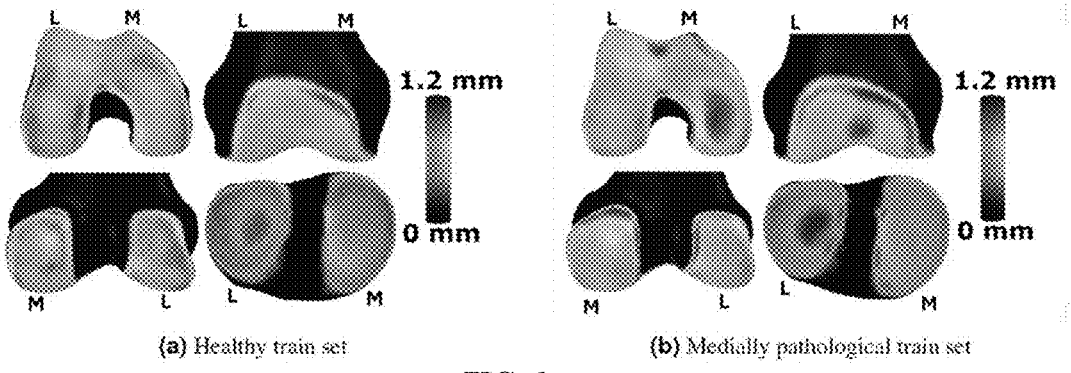
FIG. 6 represents maps of cartilage thickness standard deviation, for healthy and pathological patients of the train set. Lateral and medial sides are indicated by the letter L and M; (a) healthy train set (b) medially pathological train set.

2.2. Cartilage thickness: Mean cartilage thickness maps are presented in FIG. 5. Mean thickness distribution on the subchondral bone ranges between 0 and 3.63 or 3.79 mm for healthy and pathological femurs respectively, and between 0 and 3.20 or 3.24 mm for healthy and pathological tibias. Overall mean values are 1.86, 1.87, 1.14 and 1.06 mm for healthy and pathological femurs and tibias. Thickness standard deviation was also computed for each subchondral point and is represented in FIG. 6, with values for maximum scale at 1.01, 1.17, 0.99, and 1.17 mm. Finally, 95th percentiles of cartilage thickness are up to 4.7 mm for healthy femurs and tibias, and 4.6 mm for pathological ones.

Figure 7:
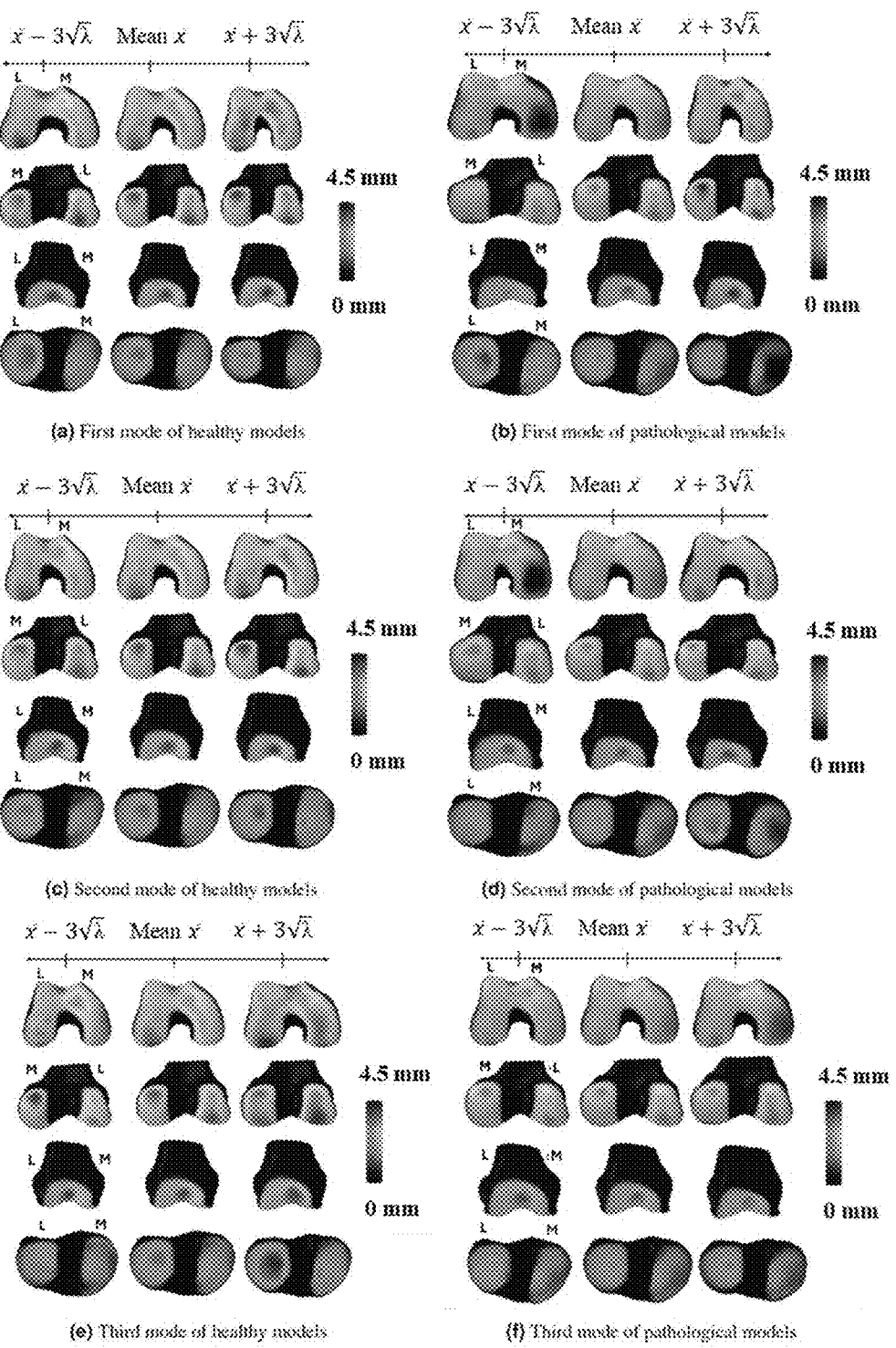
FIG. 7 represents first three variation modes of all four models, for extreme shapes represented as the mean shape±3 $\sqrt{\lambda}$. Changes in cartilage thickness distribution are displayed using a thickness map. Views are, from top to bottom: femur distal, femur posterior, femur anterior, tibia distal. Lateral and medial sides are indicated by the letter L and M; (a) First mode of healthy models (b) First mode of pathological models (c) Second mode of healthy models (d) Second mode of pathological models (e) Third mode of healthy models (f) Third mode of pathological models.

2.3. SSM modes: The first three modes of both healthy and pathological models, for femur and tibia, are gathered in FIG. 7. Extreme "plausible" shapes are plotted as the mean shape plus or minus $3\sqrt{\lambda_i}$, with $i\in[1,2,3]$ the first three principal modes of variation. The first mode is quite similar between healthy and pathological models, with condyles that get closer together and a cartilage thickness that increases for femurs and decreases for tibias. The second mode of the pathological model features an increase of condyles' width and intercondylar distance. Cartilage thickness again increases for femurs and decreases for tibias, especially on the medial side. However, no clear pattern can be distinguished on the healthy model. Finally, the third mode of the healthy model displays an increase in condyles' width and cartilage thickness on both femur and tibia and both medial and lateral sides. The pathological model only shows a decrease in cartilage thickness on femur medial side.

Figure 8:
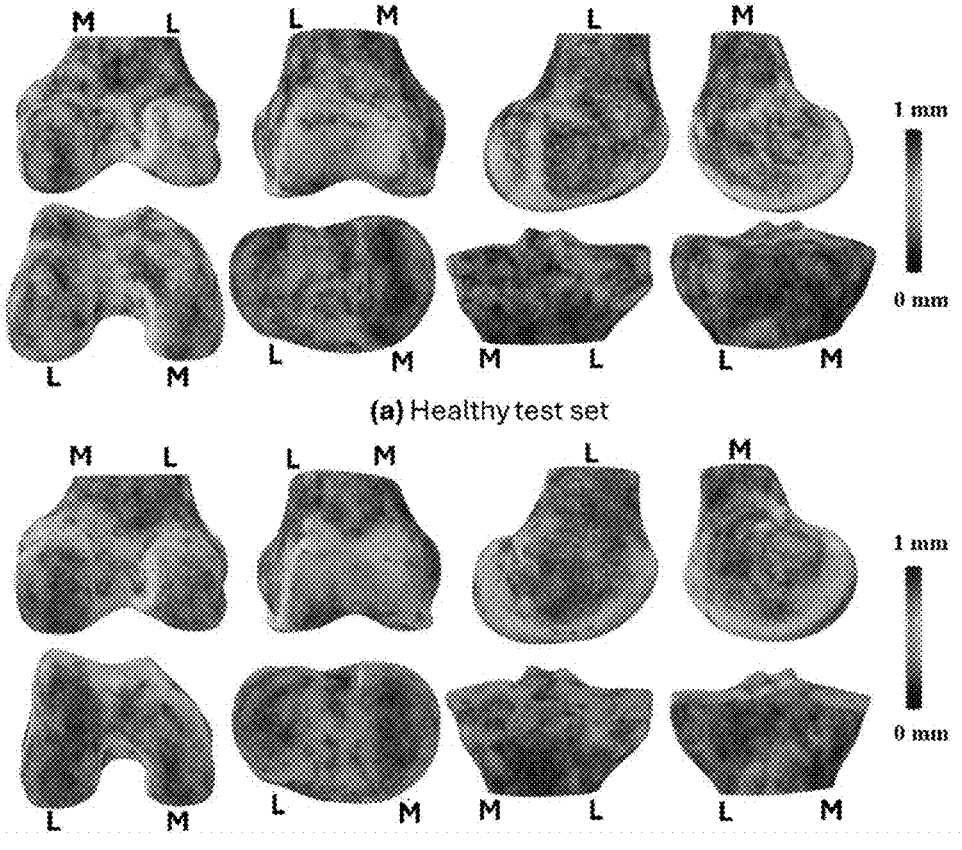
FIG. 8 represents median error map of bone fitting for healthy and pathological test sets. Lateral and medial sides are indicated by the letter L and M; (a) healthy test set (b) pathological test set.

2.4. Bone fitting: Median error maps for bone fitting are presented in FIG. 8. Median error goes up to 0.92 and 0.98 mm for healthy and pathological femurs, and up to 0.78 and 0.83 mm for healthy and pathological tibias. Median values are 0.32, 0.34, 0.28 and 0.30. 95th percentile values are 1.08, 1.15, 0.90 and 1.02 mm. It shows that the bone fitting error increases between healthy and pathological patients. Maps show that error is essentially located on the edge of the subchondral bone, were osteophytes are often located.

2.5. Cartilage prediction: Cartilage prediction results are presented in FIG. 9. Median errors equal 0.48 and 0.46 mm for healthy and pathological femurs and 0.40 and 0.44 mm for healthy and pathological tibias. Some patients have a median error value that can go up to 0.97 mm for healthy femurs and 0.71 mm for pathological tibias. Maximum values on the error maps are 0.98 and 1.0 mm for healthy and pathological femurs and 0.92 and 0.86 mm for healthy and pathological tibias. Errors are essentially localized on the trochlea and tibial lateral plateau for both healthy and pathological cases. The pathological femur also has more error on the posterior side of the medial condyle.

Figure 10:
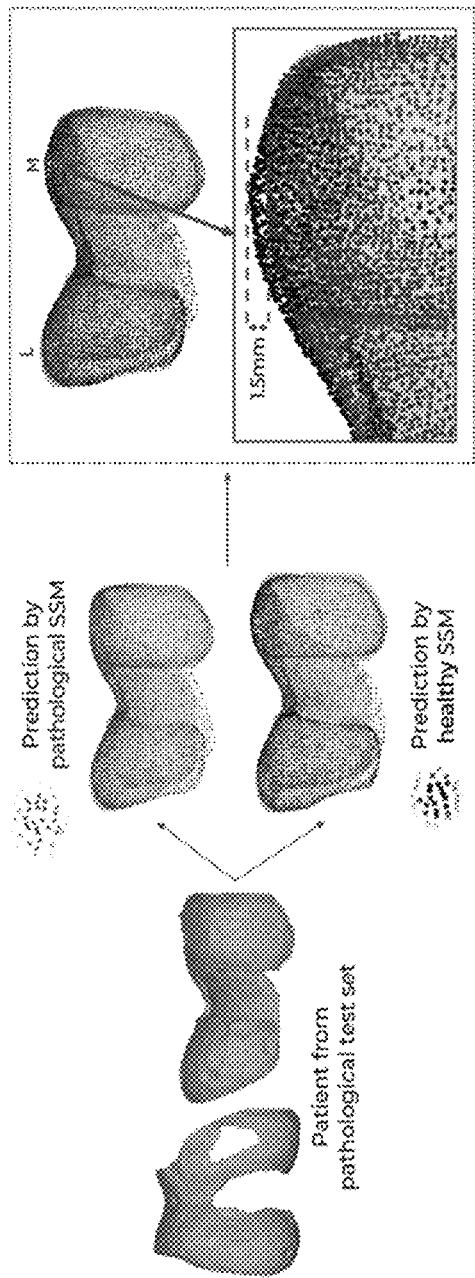
FIG. 10 represents testing match between data and models: example of the pathological case. Both healthy and pathological models are fitted to a patient from the pathological test set. Lateral and medial sides are indicated by the letter L and M.
Figure 11:
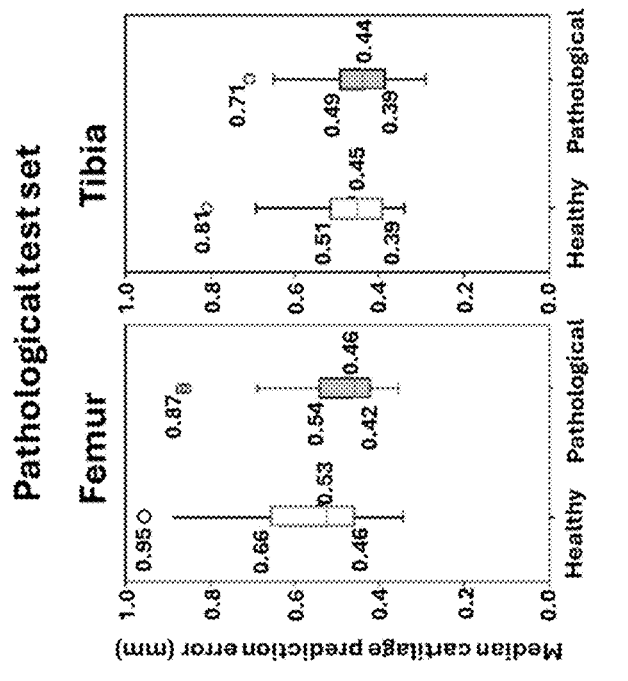
FIG. 11 represents a comparison of cartilage prediction for the healthy (left) and pathological (right) test sets, by both healthy and pathological models. Grey filled boxes indicate the match between the test set and the model (a) Healthy test set (b) Pathological test set.
Figure 11:
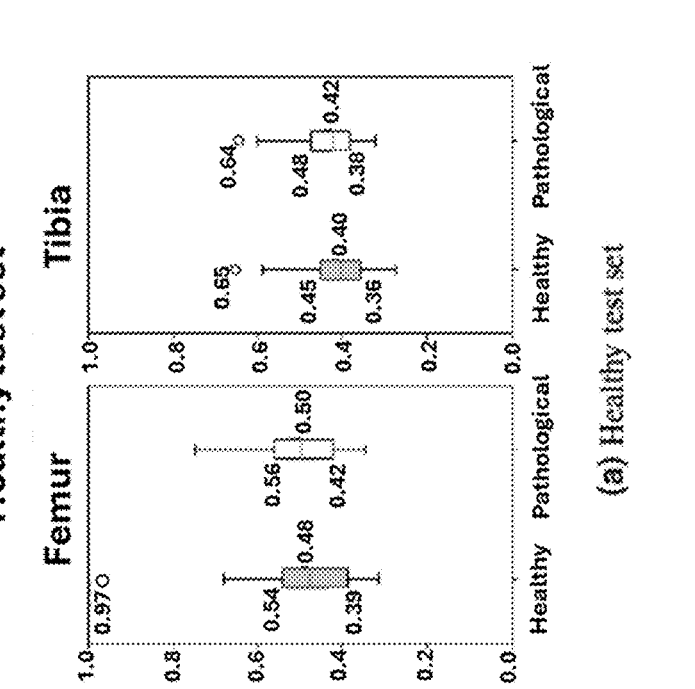

2.6. Match between data and models: The matching between training data and resulting models was assessed by fitting both healthy and pathological models to both the healthy and pathological test sets, as explained in FIG. 10 which features the pathological case. Both predicted point clouds are then compared to the ground truth. In this example, the healthy model wrongly predicted a higher cartilage thickness on the medial side, with a difference up to 1.5 mm as compared to the prediction of the pathological model. The prediction difference on the lateral side was lower, with a 0.3 mm maximal distance between points predicted by the healthy and pathological models. The prediction from the pathological model doesn't perfectly fit as well, especially on the hole because it is very patient-specific and hard to predict statistically. Quantitative results are presented in FIG. 11, where the point-to-surface distance was computed between each prediction and the corresponding ground-truth mesh. Median for each patient was then computed. The green boxes correspond to the cases where the pathology of the model matches the pathology of the patients: healthy model prediction for healthy test set, same for pathological patients. It is observed that the best prediction is always performed by the model corresponding to the test set. This difference in prediction precision is more distinct for the pathological femur where the median error goes from 0.53 mm to 0.46 mm between prediction from healthy and pathological model. For the other cases, it is rather observed an improvement of 0.01-0.02 mm in the median, but an increase in outliers' errors for the healthy test set.

3. Discussion

This example presents a solution for inferring cartilage distribution solely from bone information, for healthy and

Figure 4:
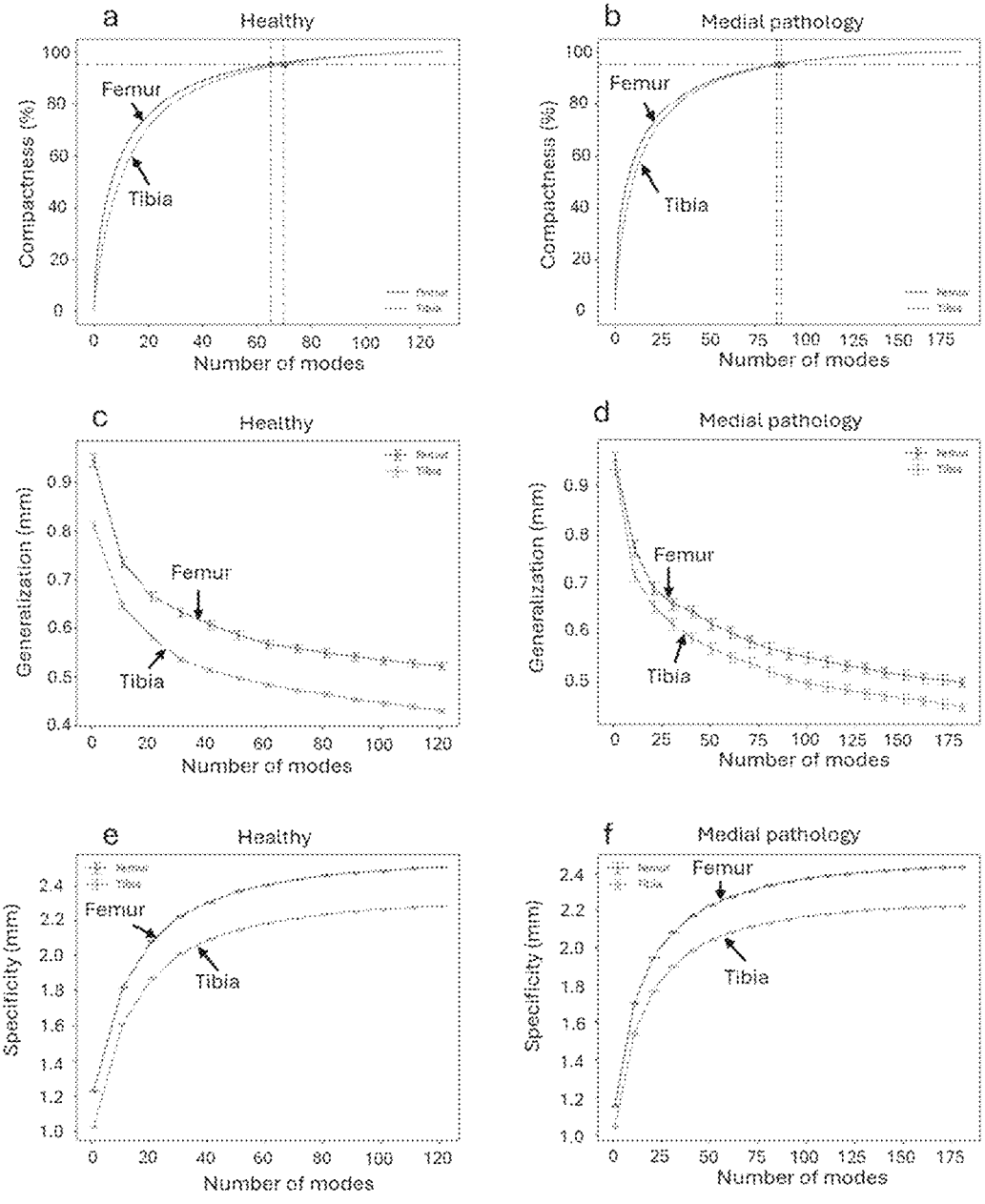
FIG. 4 represents SSM validation metrics for both healthy (left) and pathological (right) models. Error bars on generalization and specificity represent standard error values. Dotted lines in compactness represent the number of modes needed to reach 95% of explained variance.
Figure 9:
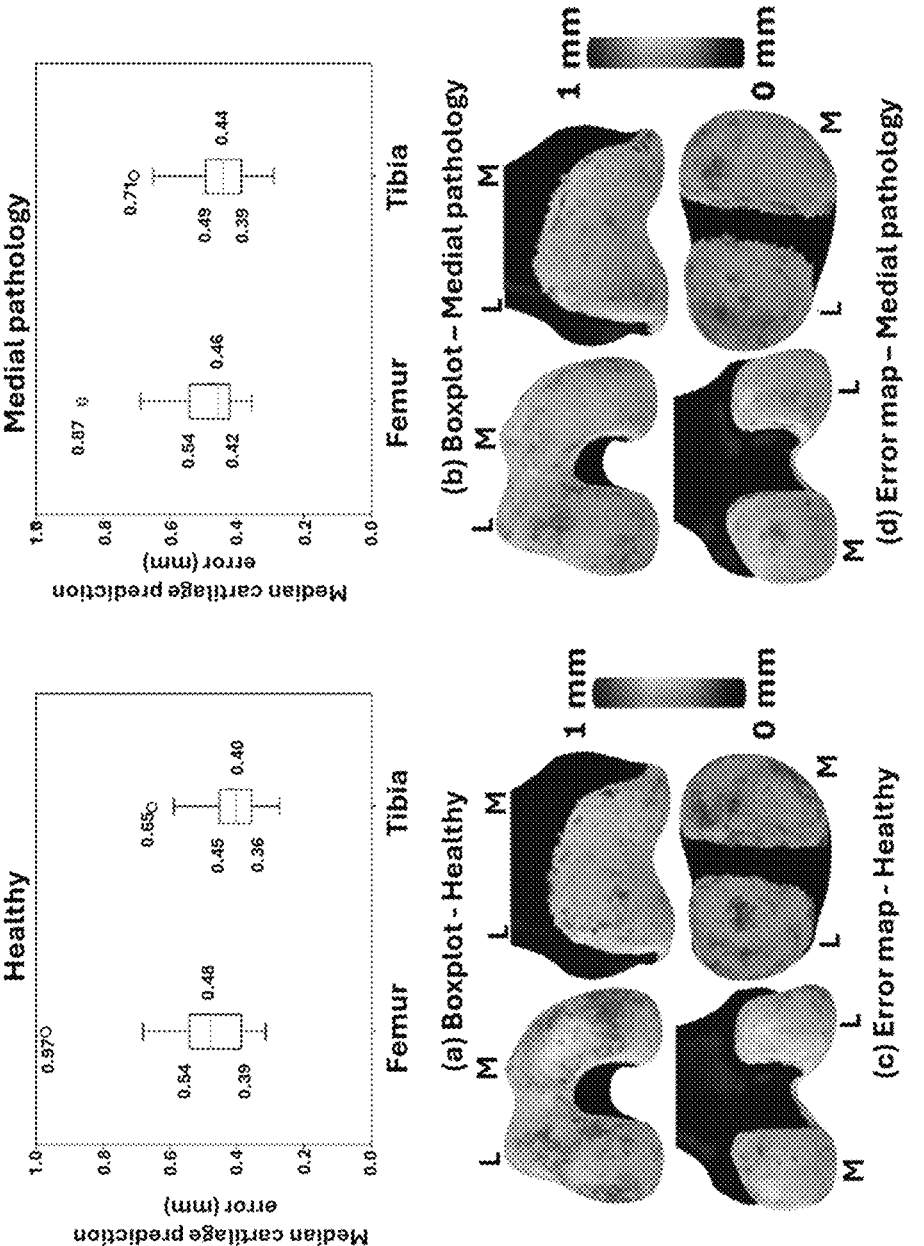
FIG. 9 represents cartilage prediction error for the healthy (left) and pathological (right) test sets. Color maps are computed from the median error for each vertex of the mean SSM mesh over all patients. Boxplots are computed from the median error for each patient over all vertices. Lateral and medial sides are indicated by the letter L and M; (a) Boxplot—Healthy (b) Boxplot—Medial pathology (c) Error map—Healthy (d) Error map—Medial pathology.

26 arthritic knees. This enables the use of CT-based robotic systems or PSIs, which reduces the cost of the TKA procedure and the impact on hospital routines with respect to MRIs. The constructed Statistical Shape Models were first verified by metrics of compactness, generalization and specificity (FIG. 4). Both generalization and specificity values are lower for the tibia than for the femur. It correlates with the simpler shape of the tibia, as compared to the femur which divides in two condyles and articulates with the patella. Metrics are quite similar between healthy and pathological models, which suggests a good adaptation of the method to the pathological shapes. Our results are coherent with the literature: generalization that converges around 0.4 and 0.3 mm for femur and tibia respectively, specificity of 2.21 and 2.14 mm for femur and tibia. However, the compactness and especially the number of modes needed to explain 95% of variance is higher than usually reported. For example, in a study only 10 and 16 modes are needed for femur and tibia, which can be explained by both the statistical modeling of bone only and the exclusion of severe KOA cases based on the presence of osteophytes. As a comparison, the training data used in this example features a majority of patients with a definite osteophytes' evidence of OARSI grade 1-3, even for patients considered healthy (table 3). This adds variability as osteophytes and cartilage loss are patient-specific and can be found in various locations around the joint, with various amplitudes. Cartilage thickness maps also demonstrated coherence with literature, with mean thickness values around 1.8-1.9 mm for femur and 1-1.2 mm for tibia, that can go up to 4 mm in some locations. As in another study, it is observed thicker cartilage on the trochlea and the weight-bearing areas of the condyles. Moreover, there is a significant decrease in cartilage thickness on the medial side between healthy and pathological sets, particularly distinct on the femoral condyle. It confirms that patients with medial KOA tend to have a cartilage loss in that area. This is corroborated by the standard deviation maps which show higher variability on the pathological set, probably because KOA affects patients in a different manner. High variability on the femoral medial condyle for pathological patients suggests various degrees of cartilage loss on that area among the set, confirmed by the dataset distribution. However, variability on the lateral tibial plateau is more difficult to interpret, and may be explained by the few patients with 2-1 medial pathology (table 1). Finally, high standard deviation on the edge of the subchondral region can be explained by the fact that the delineation of this region naturally varies widely from one patient to another, especially with the appearance of osteophytes. Finally, the first three modes for both healthy and pathological models were studied, which allowed for a better understanding of the variability captured by the four SSMs. Cartilage loss on the medial side is particularly featured on all three modes of the pathological model, for both femur and tibia. For the healthy models, the cartilage variability is more diffuse on the overall subchondral surface and seen only on the first and third modes. Furthermore, it is observe a change in the condyle width: the maximal condyle width seems higher for the pathological model. This can be explained by the appearance of osteophytes on the medial and lateral edges of the subchondral bone, to increase the contact area and better distribute the joint pressure. Finally, it is observed variability in the sizes of the intercondylar fossa on the femur and intercondylar eminence on the tibia, which is inherent to human anatomy variability. Once the SSM is validated, its fitting and prediction abilities can be assessed. As explained, the aim of this example is to generate a bone and cartilage surface as accurate as possible solely from a CT bone segmentation, that could be used as a 3D joint model for planning of TKA procedures using robotic systems or PSIs. For the bone fitting part, errors are higher on the femur than on the tibia, and for pathological rather than healthy patients. Errors are mostly located on the edge of the subchondral area, where osteophytes are often located, with an increased amplitude for the pathological case. This suggests that SSMs can only model variability to a certain extent, and that patient-specific shapes such as osteophytes can't be perfectly fitted as they are very different from one patient to another. Also, the deformation ability of the non-rigid registration model—used for SSM generation (2.2)—is restricted and can't exactly deform the template shape to fit each training patient. This ensures correct correspondences' establishment but limits the bone modeling. Fortunately, the bone surface modeling of the overall fitted shape can later be improved by post-processing using the bone segmentation which more accurately fits to osteophytes. This technique was not used in this example in order to focus on cartilage modeling. The inference of the cartilage surface is a more challenging task as it needs to predict an unseen shape that can't later be post-processed. The median prediction errors are between 0.4 and 0.5 mm, with a maximum value up to 0.97 mm. The errors are quite similar between healthy and pathological cases, which suggests that the model adapts well to the pathology. It can also be explained by the fact that, although pathology increased the variability—as seen with the compacity—, the pathological model was trained on more data and thus learnt more variability than the healthy model. The highest median error on the overall subchondral region is of 1.0 mm on the femur and 0.92 mm on the tibia. It is far below the maximal cartilage thickness of 3.61 and 6.25 mm (femur and tibial plateaus) reported in literature and the cartilage thickness 95th percentiles of 4.7 mm observed in this study (3.2). It is thus a considerable improvement as compared to a simple CT scan model that would only consider the segmented bone and omit the cartilage in the overall 3D joint model. Moreover, the median results are close to the 0.36 mm MRI resolution and below the 0.7 mm slice thickness. This resolution sets an upper limit for the model accuracy as it defines the smallest details that can be captured. An error below this resolution means that the prediction is close to the ground-truth with a precision that is below the precision of the ground-truth itself. Finally, these results outperform the inter-observer MR manual segmentation variability of existing studies, which means that predicting cartilage from a CT-scan segmentation and a SSM is a better option than segmenting it on MRI directly. The prediction errors are slightly higher when fitting the opposite SSM (i.e., fitting the healthy model on the pathological test set and vice versa). The maximal disparity between matching and opposite SSMs is observed for the pathological femurs, with a difference of 0.07 mm between the median errors of the healthy (0.53 mm) and pathological (0.46 mm) models and a maximal median value at 0.95 mm instead of 0.87 mm. Looking at some cases qualitatively (FIG. 10), this can be explained by a better prediction on the medial side: the pathological model predicts a thinner cartilage surface on the medial side, which better match the pathological cartilage distribution. However, it is seen that the hole in the cartilage wasn't predicted, most likely because it is very patient-specific and isn't directly related to the bone shape. The impact on the lateral side is less visible, with similar thicknesses predicted by both models. Overall, the differences in the quantitative results remain quite small, which questions the necessity for two different models. It would be interesting to generate a global SSM trained on both the healthy and pathological datasets, to see if the bone shape is enough to predict either a healthy or pathological cartilage distribution. This study has several limitations. First of all, two models that were trained on a different number of patients were compared. This choice was motivated by the wish to use as many patients as available, but may impact the comparison results. In this regard, patients with lateral or bilateral pathologies were not studied because the dataset size was considered insufficient to train a SSM. Nonetheless, it would be interesting to study these pathologies and see if the same conclusions as those presented here can be drawn. Second, the aim is to predict cartilage from a bone model obtained by CT-scan segmentation. However, the cartilage prediction was only tested on bone MRI segmentations. There may be a bias between MR and CT bone surfaces, that would lead to different cartilage thicknesses when predicted from CT bone. A paired MRI-CT database would be of particular interest to test this hypothesis. Third, the choice of the JSN criteria to create several models is questionable, especially for CT-based cartilage prediction as CT scan is a non weight-bearing imaging modality. The inter-osseous distance might be overestimated as compared to the real cartilage thickness. Also, the inter-observer variability in correctly estimating JSN from CT scan would be interesting to study. In this example, the JSN OARSI grade estimation was based on X-ray, which is a weight-bearing modality and thus might not transfer well to CT scan. Finally, this study doesn't check that femur and cartilage predictions don't intersect. A tibiofemoral model could prevent it (only on the bones; or on bone and cartilage). This model could also include the patella, which could improve the cartilage prediction on the trochlea where most errors are located (FIG. 9).

The invention claimed is:

1. A device for obtaining an augmented patient-specific bone/cartilage model of a target anatomical structure of a patient, said target anatomical structure including at least one portion of a target bone and at least one portion of a target cartilage, said device comprising:
   at least one input configured to receive:
      a dataset comprising 3D images acquired on a plurality of subjects, each 3D image acquired on a subject comprising a subject anatomical structure corresponding to the target anatomical structure, wherein each of said 3D images comprise bone tissues of the subject anatomical structure and at least part of each of said 3D images comprise cartilage tissues of the subject anatomical structure, and
      a previously generated patient-specific 3D model of at least one portion of said target bone of the patient;
   at least one processor configured to:
      for at least two 3D images of the dataset, segment the bone tissues of the subject anatomical structure,
      determine a bone Statistical Shape Model based on said segmented bone tissues,
      for at least two 3D images of the dataset comprising cartilage tissues of the subject anatomical structure, segment the subject anatomical structure and perform a rigid registration of said bone Statistical Shape Model with the segmented bone tissues of the subject anatomical structure and optimize at least one parameter of said bone Statistical Shape Model to correspond with said bone tissues so as to obtain a global dataset comprising the optimized bone Statistical Shape Model associated with the cartilage tissues from the segmented subject anatomical structure, determine a global Statistical Shape Model of the subject anatomical structure based on said global dataset, said global Statistical Shape Model including a bone portion and a cartilage portion, perform a rigid registration of the bone portion from said global Statistical Shape Model with said patient-specific 3D model and optimize at least one parameter of said global Statistical Shape Model to correspond with said patient-specific 3D model, and generate said augmented patient-specific bone/cartilage model of the target anatomical structure based on the optimized global Statistical Shape Model registered with said patient-specific 3D model.

2. The device according to claim 1, wherein said dataset comprises:

a first ensemble comprising 3D images acquired from a plurality of subjects, said 3D images comprising bone tissues from the subject anatomical structure, and a second ensemble comprising 3D images acquired from a plurality of subjects, said 3D images comprising bone tissues and cartilage tissues from the subject anatomical structure.

3. The device according to claim 1, wherein the at least one input is further configured to receive at least one 3D image acquired from at least one 3D image sensor during surgery, wherein said at least one 3D image represents at least one exposed portion of the target anatomical structure, and wherein the at least one processor is further configured to register and optimize at least one parameter of the augmented patient-specific bone/cartilage model associated to the cartilage with the at least one exposed portion of the target anatomical structure of the 3D image.

4. The device according to claim 3, wherein registering and optimizing the at least one parameter of the augmented patient-specific bone/cartilage model is achieved by minimizing a cost function that takes into account the at least one parameter of the augmented patient-specific bone/cartilage model and localization parameters.

5. The device according to claim 1, wherein determining said global Statistical Shape Model comprises:

defining a plurality of vectors being normal to at least one portion of a surface of said optimized bone Statistical Shape Model of the global dataset;

for each of the segmented cartilage of the global dataset, obtaining a first and a second intersection between each of said plurality of vectors and said segmented cartilage; and determining said global Statistical Shape Model using said first and second intersections, obtained from the plurality of segmented cartilages of the global dataset, and the optimized bone Statistical Shape Model of the global dataset.

6. The device according to claim 1, wherein the at least one input is further configured to receive at least one thickness measurement performed on a predetermined position on the cartilage, and wherein the processor is further configured to constrain the optimization of the at least one parameter of the global Statistical Shape Model associated to the cartilage based on the at least one measurement so as to generate an updated augmented patient-specific bone/cartilage model.

7. The device according to claim 1, wherein the at least one input is further configured to receive at least one metadata, and wherein the processor is further configured to constrain the optimization of the at least one parameter of the global Statistical Shape Model based on the at least one metadata so as to generate an updated augmented patient-specific bone/cartilage model.

8. The device according to claim 1, wherein said at least one processor is further configured to use said augmented patient-specific bone/cartilage model to guide an orthopedic surgery guidance system.

9. A computer implemented method for obtaining an augmented patient-specific bone/cartilage model of a target anatomical structure of a patient, said target anatomical structure including at least one portion of a target bone and at least one portion of a target cartilage, said method comprising:

receiving:

a dataset comprising 3D images acquired on a plurality of subjects, each 3D image acquired on a subject comprising a subject anatomical structure corresponding to the target anatomical structure, wherein said 3D images comprise bone tissues of the subject anatomical structure and at least part of said 3D images comprise cartilage tissues of the subject anatomical structure, and a previously generated patient-specific 3D model of at least one portion of said target bone of the patient;

for at least two 3D image of the dataset, segmenting the bone tissues of the subject anatomical structure, determining a bone Statistical Shape Model based on said segmented bone tissues, for at least two 3D image of the dataset comprising cartilage tissues of the subject anatomical structure, segmenting the subject anatomical structure and performing a rigid registration of said bone Statistical Shape Model with the segmented bone tissues of the subject anatomical structure and optimizing at least one parameter of said bone Statistical Shape Model to correspond with said bone tissues so as to obtain a global dataset comprising the optimized bone Statistical Shape Model associated with the cartilage tissues from the segmented subject anatomical structure, and determining a global Statistical Shape Model of the at least one portion of target bone and target cartilage of the target anatomical structure based on said global dataset, said global Statistical Shape Model including a bone portion and a cartilage portion, performing a rigid registration of the bone portion from said global Statistical Shape Model with said patient-specific 3D model and optimizing at least one parameter of said global Statistical Shape Model to correspond with said patient-specific 3D model, and generating said augmented patient-specific bone/cartilage model of the target anatomical structure based on the optimized global Statistical Shape Model registered with said patient-specific 3D model.

10. The computer implemented method according to claim 9, wherein said dataset comprises:

a first ensemble comprising 3D images acquired from a plurality of subjects, said 3D images comprising bone tissues from the subject anatomical structure, and a second ensemble comprising 3D images acquired from a plurality of subjects, said 3D images comprising bone tissues and cartilage tissues from the subject anatomical structure.

11. The computer implemented method according to claim 9, further comprising:

receiving at least one 3D image acquired from at least one 3D image sensor during surgery, wherein said at least one 3D image represents at least one exposed portion of the target anatomical structure, registering and optimizing at least one parameter of the augmented patient-specific bone/cartilage model associated to the cartilage with the at least one exposed portion of the target anatomical structure of the 3D image.

12. The computer implemented method according to claim 11, wherein registering and optimizing the at least one parameter of the augmented patient-specific bone/cartilage model is achieved by minimizing a cost function that takes into account the at least one parameter of the augmented patient-specific bone/cartilage model and localization parameters.

13. The computer implemented method according to claim 9, wherein determining said global Statistical Shape Model comprises:

defining a plurality of vectors being normal to at least one portion of a surface of said optimized bone Statistical Shape Model of the global dataset;

for each of the segmented cartilage of the global dataset, obtaining a first and a second intersection between each of said plurality of vectors and said segmented cartilage; and determining said global Statistical Shape Model using said first and second intersections, obtained from the plurality of segmented cartilages of the global dataset, and the optimized bone Statistical Shape Model of the global dataset.

14. The computer implemented method according to claim 9, further comprising:

receiving at least one thickness measurement performed on a predetermined position on the cartilage, constraining the optimization of the at least one parameter of the global Statistical Shape Model associated to the cartilage based on the at least one measurement so as to generate an updated augmented patient-specific bone/cartilage model.

15. The computer implemented method according to claim 9, further comprising:

receiving at least one metadata, constraining the optimization of the at least one parameter of the global Statistical Shape Model based on the at least one metadata so as to generate an updated augmented patient-specific bone/cartilage model.

16. The computer implemented method according to claim 9, further comprising using said augmented patient-specific bone/cartilage model to guide an orthopedic surgery guidance system.

17. A non-transitory program storage device, readable by a computer, tangibly embodying a program of instructions executable by the computer to perform the method according to claim 9.

18. A non-transitory computer-readable medium comprising instructions which, when executed by a computer, cause the computer to carry out the method according to claim 9.

* * * * *